US008481175B2

(12) United States Patent
Ooishi et al.

(10) Patent No.: US 8,481,175 B2
(45) Date of Patent: Jul. 9, 2013

(54) OLIGOFLUORENE COMPOUND AND ORGANIC EL ELEMENT USING SAME

(75) Inventors: Ryota Ooishi, Yokohama (JP); Takao Takiguchi, Chofu (JP); Jun Kamatani, Tokyo (JP); Tetsuya Kosuge, Kawasaki (JP); Shigemoto Abe, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 602 days.

(21) Appl. No.: 12/261,765

(22) Filed: Oct. 30, 2008

(65) Prior Publication Data

US 2009/0115323 A1 May 7, 2009

(30) Foreign Application Priority Data

Nov. 1, 2007 (JP) ................................. 2007-284830

(51) Int. Cl.
*H01L 51/54* (2006.01)

(52) U.S. Cl.
USPC ........... 428/690; 313/504; 313/505; 313/506; 428/917; 257/40; 257/E51.05; 257/E51.032; 528/394; 528/397; 528/422

(58) Field of Classification Search
USPC ..... 428/690, 917; 313/504, 505, 506; 257/40, 257/E51.05, E51.032; 528/394, 397, 422
See application file for complete search history.

(56) References Cited

U.S. PATENT DOCUMENTS

| | | | |
|---|---|---|---|
| 5,708,130 A * | 1/1998 | Woo et al. ...................... 528/397 |
| 2004/0253389 A1 * | 12/2004 | Suzuki et al. .................. 428/1.1 |
| 2005/0191927 A1 * | 9/2005 | Gambogi et al. ............... 445/24 |
| 2006/0066225 A1 * | 3/2006 | Kishino et al. ................. 313/504 |

FOREIGN PATENT DOCUMENTS

| | | |
|---|---|---|
| JP | 2004-083481 A | 3/2004 |
| JP | 2006-128632 A | 5/2006 |
| JP | 2007-204425 * | 8/2007 |

OTHER PUBLICATIONS

W. Helfrich and W.G. Schneider, "Recombination Radiation in Anthracene Crystals", Physical Review Letters, vol. 14 No. 7, pp. 229-331, 1964.
C.W. Tang and S.A. VanSlyke, "Organic Electroluminescent Diodes", Appl. Phys. Lett. 51 (12), Sep. 21, 1987, pp. 913-915.

(Continued)

*Primary Examiner* — Jennifer Chriss
*Assistant Examiner* — Gregory Clark
(74) *Attorney, Agent, or Firm* — Canon U.S.A., Inc., IP Division

(57) ABSTRACT

An oligofluorene compound is represented by the General Formula (1) below

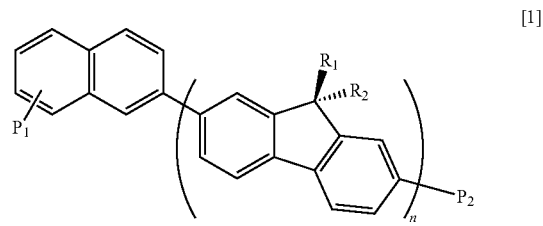

wherein in Formula (1) $P_1$ represents a hydrogen atom, a halogen atom, or a linear or branched alkyl group having 1 to 20 carbon atoms; $P_2$ represents a hydrogen atom, a halogen atom, a substituted or unsubstituted linear or branched alkyl group having 1 to 20 carbon atoms, a substituted or unsubstituted phenyl group, or a substituted or unsubstituted 2-naphthyl group; $R_1$ and $R_2$ each represent a hydrogen atom, a halogen atom, or a linear or branched alkyl group having 1 to 20 carbon atoms; and n represents integer of 2 to 4.

9 Claims, 1 Drawing Sheet

OTHER PUBLICATIONS

M.A. Baldo et al., "Very high-efficiency green organic light-emitting devices based on electrophosphorescence", Applied Physics Letters, vol. 75 No. 1, Jul. 5, 1999, pp. 4-6.

Chihaya Adachi et al., "High-efficiency red electrophosphorescence devices", Applied Physics Letters, vol. 78 No. 11, Mar. 12, 2001, pp. 1622-1624.

Norio Miyaura and Akira Suzuki, "Palladium-Catalyzed Cross-Coupling Reactions of Organoboron Compounds", Chem. Rev. Jan. 31, 1995, pp. 2457-2483.

Takakazu Yamamoto et al., "A Novel Type of Polycondensation Utilizing Transition Metal-Catalzyed C-C Coupling", Bulletin of the Chemical Society of Japan, vol. 51 (7), Jan. 21, 1978, pp. 2091-2097.

* cited by examiner

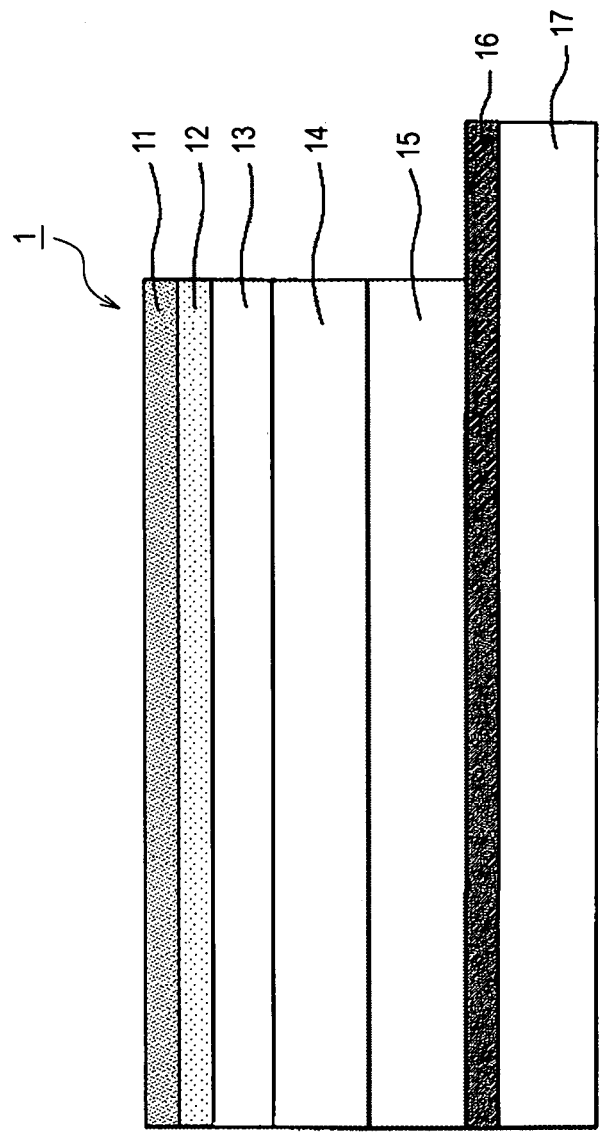

OLIGOFLUORENE COMPOUND AND ORGANIC EL ELEMENT USING SAME

BACKGROUND OF THE INVENTION

1. Field of the Invention

The present invention generally relates to an oligofluorene compound and an organic EL element using same.

2. Description of the Related Art

Organic electroluminescence elements (referred to hereinbelow as organic EL elements) are presently actively studied for use in planar light-emitting sources and thin display panels.

An organic EL element is typically composed of two electrodes and a multilayer thin film of an organic amorphous charge transport material sandwiched between the two electrodes. The drive principle of the organic EL element resides in the excitation of molecules contained in the thin film by injecting carriers, namely holes and electrons, from the electrodes into the thin film and causing the recombination of the carriers. The excited molecules then decay. Light emission occurs in this decay process and the emitted light passes to the outside of the element.

Light emission induced by voltage application to an anthracene single crystal (W. Helfrich Phys. Rev. Lett. 14, 229 (1964)) and light emission from a two-layer thin film of an organic amorphous charge transport material discovered by Tang et al. (Appl, Phys. Lett. 51, 913 (1987)) were reported a long time ago. Light emission from a double hetero structure (three-layer structure) composed of a hole transport layer, a light-emitting layer, and an electron transport layer disclosed in M. A. Baldo et al. Appl. Phys. Lett. 75, 4 (1999) has recently been suggested.

As another example, fluorescent light-emitting materials that use only a singlet exciton component and phosphorescent light-emitting materials using both singlet excitons and triplet excitons as a light emission source have been suggested as light-emitting materials. According to a spin selection rule, excitons generated by recombination of carriers are generated at a ratio of singlet excitons to triplet excitons of 1:3. The phosphorescent light-emitting materials can use both the generated singlet excitons and the generated triplet excitons as light emission sources. Therefore, the theoretical internal quantum efficiency of phosphorescence light-emitting materials is 100%, which is highly desirable for high-efficiency organic EL elements.

As described hereinabove, where a phosphorescent light-emitting material is used as a constituent material of an organic EL element, the efficiency in principle can be increased over that of other conventional fluorescent light-emitting materials. However, a sufficiently high light emission efficiency presently cannot be realized. For example, an organic EL element has been disclosed (Chihaya Adachi et al. Appl. Phys. Lett. vol. 78, 1622 (2001)) that uses $(Btp)_2Ir$ (acac), which uses a phosphorescent light-emitting material as a guest material and a well-known compound CBP as a host material. According to the disclosure, the maximum external quantum yield obtained by the combination of CBP and $(Btp)_2Ir(acac)$ is about 7%. Therefore, there remains a need for combinations of host materials and guest materials (dopant materials) that are capable of increasing the light emission efficiency.

Furthermore, the conventional design and selection of host materials for use with the phosphorescent light-emitting dopants have often been focused on obtaining a sufficiently high triplet energy, so as to inhibit a reverse energy transition from the triplet energy of a dopant to the triplet energy of a host. However, the effects of other physical parameters of host materials have not as yet been sufficiently studied.

Accordingly, the efficiency and decrease in voltage of organic EL elements are presently insufficient, and there remains a need for organic EL elements that have better light emission efficiency and can be driven by a lower voltage. Further, service life of organic EL elements is presently also insufficient, and organic EL elements with a longer service life are needed.

SUMMARY OF THE INVENTION

In one embodiment, an oligofluorene compound in accordance with the present invention is represented by a General Formula (1) below

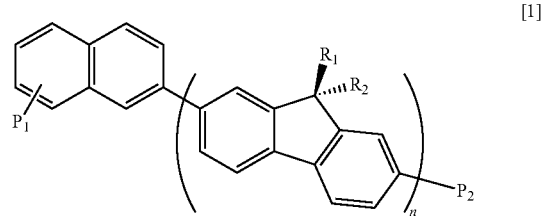

[1]

wherein in Formula (1) $P_1$ represents a hydrogen atom, a halogen atom, or a linear or branched alkyl group having 1 to 20 carbon atoms; $P_2$ represents a hydrogen atom, a halogen atom, a substituted or unsubstituted linear or branched alkyl group having 1 to 20 carbon atoms, a substituted or unsubstituted phenyl group, or a substituted or unsubstituted 2-naphthyl group; $R_1$ and $R_2$ each represent a hydrogen atom, a halogen atom, or a linear or branched alkyl group having 1 to 20 carbon atoms; and n represents an integer of 2 to 4.

Further features of the present invention will become apparent from the following description of exemplary embodiments (with reference to the attached drawings).

BRIEF DESCRIPTION OF THE DRAWINGS

FIG. 1 is a cross-sectional view illustrating an embodiment of the organic EL element in accordance with the present invention.

DESCRIPTION OF THE EMBODIMENTS

Embodiments of the present invention will be described below in greater details. For example, the oligofluorene compound in accordance with the present invention will be described below in greater details. In one version, the oligofluorene compound in accordance with the present invention is represented by the General Formula (1) below.

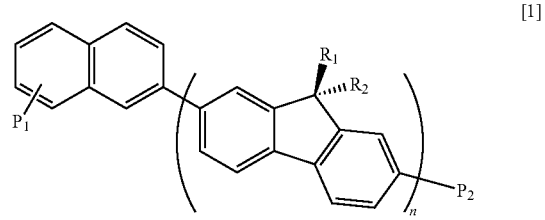

[1]

In Formula (1), $P_1$ represents a hydrogen atom, a halogen atom, or a linear or branched alkyl group having 1 to 20 carbon atoms.

Examples of the halogen atom represented by $P_1$ may include, but are not limited to fluorine, chlorine, iodine, and bromine.

Examples of the linear or branched alkyl group having 1 to 20 carbon atoms represented by $P_1$ may include, but are not limited to, a methyl group, an ethyl group, a normal propyl group, an isopropyl group, a normal butyl group, and a tertiary butyl group.

In Formula (1), $P_2$ represents a hydrogen atom, a halogen atom, a substituted or unsubstituted linear or branched alkyl group having 1 to 20 carbon atoms, a substituted or unsubstituted phenyl group, or a substituted or unsubstituted 2-naphthyl group.

Examples of the halogen atom represented by $P_2$ may include, but are not limited to, fluorine, chlorine, iodine, and bromine.

Examples of the linear or branched alkyl group having 1 to 20 carbon atoms represented by $P_2$ may include, but are not limited to, a methyl group, an ethyl group, an n-propyl group, an isopropyl group, an n-butyl group, and a tertiary butyl group.

Examples of substituents that may be present in the alkyl group, phenyl group, and 2-naphthyl group may include, but are not limited to, alkyl groups such as a methyl group, a tertiary butyl group, and an isopropyl group, aryl groups such as a phenyl group and a tolyl group, halogen atoms such as fluorine, chlorine, and bromine, and alkoxy groups such as a methoxy group and an ethoxy group.

In Formula (1), $R_1$ and $R_2$ each represent a hydrogen atom, a halogen atom, or a linear or branched alkyl group having 1 to 20 carbon atoms.

Examples of the halogen atom represented by $R_1$ and $R_2$ may include, but are not limited to, fluorine, chlorine, iodine, and bromine.

Examples of the linear or branched alkyl groups having 1 to 20 carbon atoms represented by $R_1$ and $R_2$ may include, but are not limited to, a methyl group, a trifluoromethyl group, an ethyl group, an n-propyl group, an isopropyl group, an n-butyl group, and a tertiary butyl group.

In Formula (1), n represents an integer of 2 to 4.

In one embodiment, the oligofluorene compound represented by Formula (1) corresponds to the compound represented by General Formula (2) below.

[2]

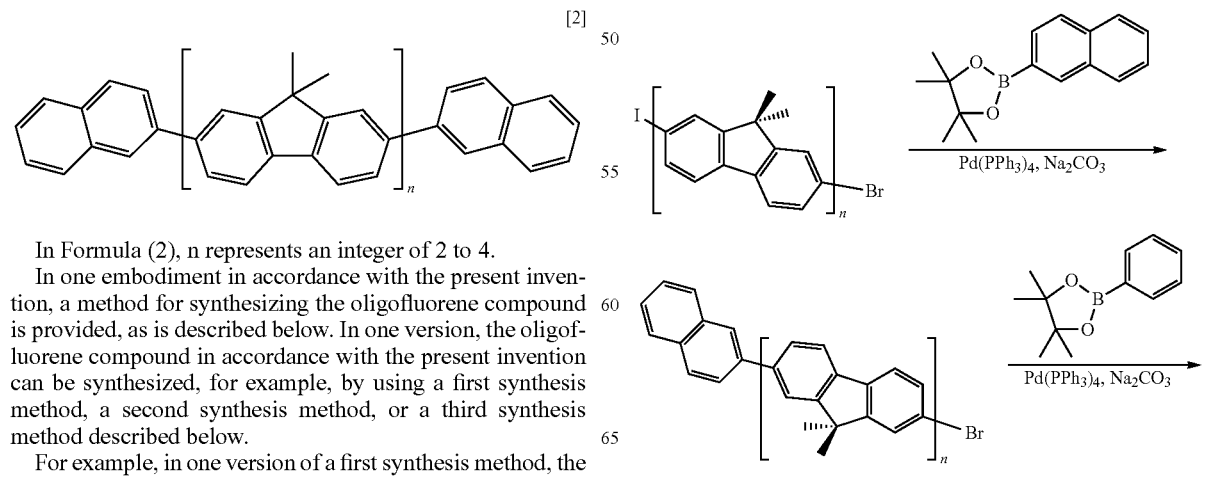

In Formula (2), n represents an integer of 2 to 4.

In one embodiment in accordance with the present invention, a method for synthesizing the oligofluorene compound is provided, as is described below. In one version, the oligofluorene compound in accordance with the present invention can be synthesized, for example, by using a first synthesis method, a second synthesis method, or a third synthesis method described below.

For example, in one version of a first synthesis method, the synthesis may be performed as shown by the reaction formula below by using a 2,7-dibromo modification of an oligofluorene (where the number of directly coupled fluorene skeletons is 2 to 4) and a 2-naphthylboronic acid derivative (such as for example a pinacol ester derivative thereof) as starting materials.

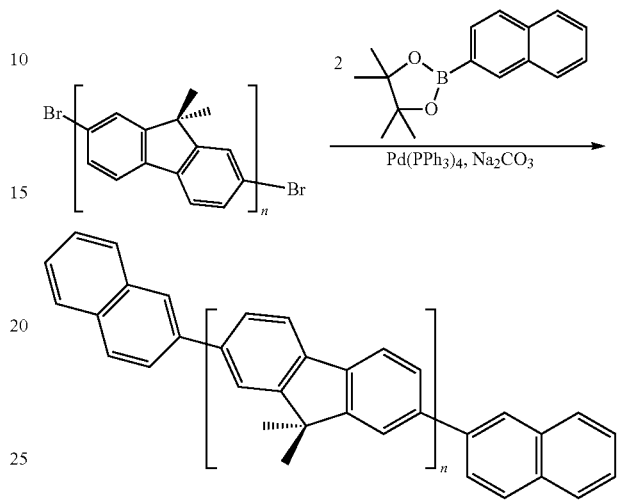

More specifically, in this version of the method, 1 eq of a 2,7-dibromo modification of an oligofluorene and 2 eq of a 2-naphthylboronic acid derivative (such as the pinacol ester) may be coupled by the Suzuki coupling reaction (see Chem. Rev. 1995, 2457-2483) via a palladium catalyst. In another version, the coupling may be also performed by the Yamamoto method (see Bull. Chem. Soc. Jpn. 51, 2091, 1978) using a nickel catalyst. In yet another version, the synthesis can be also similarly performed by using a 2,7-diboron modification of an oligofluorene and 2-bromonaphthalene.

As another example, in one version of a second synthesis method, the synthesis may be performed as shown by the reaction formula below by using a 2-bromo-7-iodo modification of an oligofluorene (with the number of directly coupled fluorene skeletons being 2 to 4) and arylboronic acid derivatives of two kinds (such as for example pinacol esters thereof) as starting materials.

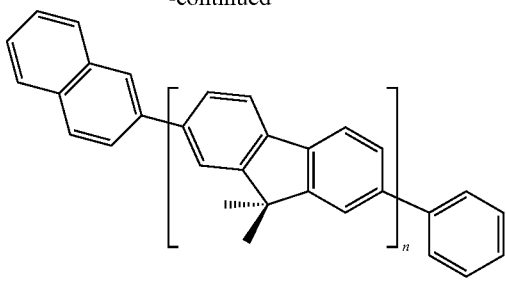

The second synthesis method may allow the substituents to be introduced asymmetrically with respect to the oligofluorene skeleton.

More specifically, in this version of the method, 1 eq of a 2-bromo-7-iodo modification of an oligofluorene and 1 eq of a 2-naphthylboronic acid derivative are first coupled by the Suzuki coupling reaction via a palladium catalyst. In this case, because of the difference in reactivity in the coupling reaction between iodine and bromine, a monobromo modification is selectively obtained. Then, an oligofluorene compound in accordance with the present invention can be synthesized by coupling 1 eq of the monobromo modification to 1 eq of a boronic acid derivative (for example, phenylboronic acid) that is different from that used in the first stage by the Suzuki coupling reaction. In another version, the coupling method also may be the Yamamoto method using a nickel catalyst.

As yet another example, in one version of a third synthesis method, the synthesis may be performed as shown by the reaction formula below by using a 2-bromo modification of an oligofluorene (with the number of directly coupled fluorene skeletons being 2 to 4) and a 2-naphthylboronic acid derivative (such as for example a pinacol ester thereof) as starting materials.

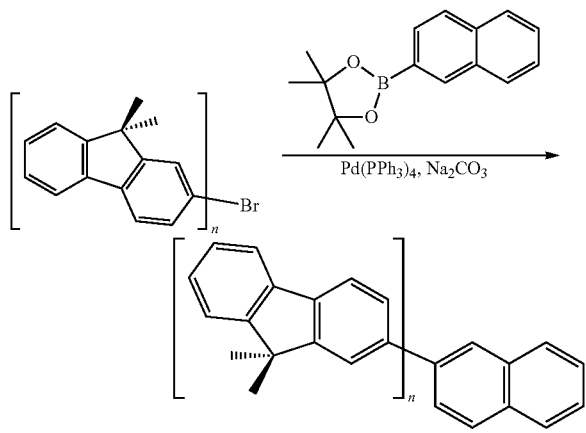

The third synthesis method may allow for example, one 2-naphthyl group to be introduced in the oligofluorene skelton.

More specifically, in this version of the method, the synthesis can be performed by coupling 1 eq of a 2-monobromo modification of an oligofluorene to 1 eq of a 2-naphthylboronic acid derivative by the Suzuki coupling reaction via a palladium catalyst. In another version, the coupling may be also performed by the Yamamoto method using a nickel catalyst.

In one embodiment of the invention, the oligofluorene compound can be used as a constituent material of an organic EL element, for example as a host material of a light-emitting layer. In one version, when the oligofluorene compound in accordance with the present invention is used as a constituent material of an organic EL element, a thin film including the oligofluorene compound in accordance with the present invention can be formed by, for example, thermal vapor deposition.

When a thin film constituting an organic EL element is formed by thermal vapor deposition, the compound contained in the thin film typically has one or more of the following properties.

(1) Capability of forming a stable amorphous film.
(2) Resistance to decomposition during thermal vapor deposition.
(3) High charge mobility.
(4) High charge injection ability.

When the thin film is a light-emitting layer composed of a host material and a guest material, and the guest material (light-emitting dopant) is a phosphorescent light-emitting material, the compound serving as a corresponding host may additionally have the following property in addition to any of the above-described properties (1) to (4).

(5) The triplet energy of the host is higher than that (triplet energy) of the guest.

The aforementioned properties (1) to (5) will be described below in greater detail in relation to the oligofluorene compound in accordance with the present invention.

Formation of Amorphous Film

Thermal vapor deposition is generally performed under high vacuum. The "high vacuum" may typically be represented by a degree of vacuum of about $10^{-3}$ to $10^{-6}$ Pa. Furthermore, in order to form a stable amorphous thin film by thermal vapor deposition under high vacuum, it may be desirable in some embodiments that the molecular weight of the compound forming the thin film be at least about 500 grams/mol and that a bulky structure (such as a bulky substituent) for inhibiting the crystallization be present in the molecular skeleton.

The stability of the amorphous thin film thus formed can be evaluated by glass transition temperature measurements using a differential scanning calorimeter (DSC). Materials with a high glass transition temperature typically can form a stable amorphous thin film. The oligofluorene compound in accordance with one version of the present invention has an alkyl group crossing a π-plane in a 9 position of a fluorenyl skeleton. As a result, the molecule itself does not have a planar structure, and the occurrence of interactions between the adjacent molecules is suppressed, whereby the crystallization of the thin film may be inhibited.

Decomposition During Thermal Vapor Deposition

In order to inhibit decomposition during thermal vapor deposition, the molecular weight of the compound forming the thin film may, in some embodiments, be a maximum of about 1500 grams/mol. This is because if the molecular weight is too high, the temperature for vapor deposition may increase, and the compound that is vapor deposited may become thermally decomposed.

Charge Mobility

For the compound that is a constituent material of an organic EL element to have a high charge mobility, the size of a π electron cloud between the molecules may be relatively large. For example, a polyacene skeleton such as naphthalene and anthracene, which has a relatively large size of a π electron cloud between the molecules, also has a relatively high charge mobility. Therefore, where a polyacene skeleton is introduced in a molecule, the size of a π electron cloud between the molecules is increased and, therefore, an increase in charge mobility can be achieved. Accordingly, because the oligofluorene compound in accordance with the present invention has at least one naphthalene site, charge mobility may be increased.

Charge Injection Ability

In order to increase the efficiency of hole and electron injection from electrodes or transport layers (charge injection ability) in organic EL elements, the energy gap (UV absorption ends of a UV spectrum of the material formed into a thin film) of a host may be narrowed, and may even be narrowed as much as possible. This may enable an increase in the number of both carriers, that is, holes and electrons, injected into the light-emitting layer.

The density of carriers injected into the light-emitting layer is determined at least in part by the relationship thereof with the energy level of the host. More specifically, the density of injected holes may be related to the HOMO (Highest Occupied Molecular Orbital) of the host, and the density of injected electrons may be related to the LUMO (Lowest Unoccupied Molecular Orbital) of the host. In one version, an effective method may be to bring the respective energy levels close to the energy level of the adjacent carrier transporting material and decrease the difference between the energy levels. In order to lower the injection barriers of holes and electrons so as to enable the injection of the two carriers, the energy difference of the two HOMO and LUMO levels may be reduced. In other words, narrowing the energy gap may in certain circumstances be most effective. On the other hand, because narrowing the energy gap of the host can increase the barrier with the HOMO level of the electron transport layer adjacent to the light-emitting layer and with the LUMO level of the hole transport layer adjacent to the light-emitting layer, in certain instances the carrier confinement effect may be observed. As a result, the injected carriers can be confined with good efficiency within the light-emitting layer and excitons can be generated within the light-emitting layer. Therefore, light emission efficiency of the element may be increased and drive voltage thereof may be decreased.

In one version, in order to narrow the energy gap of material, the skeletons having a π plane may be coupled linearly and the conjugation length of the molecule may be extended. For example, in one version of an oligofluorene compound in accordance with the present invention, one 2-naphthalene site and two or more dimethylfluorene sites may be coupled linearly, and thus the conjugation length of the entire molecule is relatively large. Therefore, the energy gap of the compound itself can be narrowed. However, in certain circumstances, when there is only one dimethylfluorene site, the energy gap may not be narrowed sufficiently.

Triplet Energy

However, when the phosphorescent light-emitting material is a light-emitting dopant, the triplet energy of the corresponding host may be higher than the triplet energy of the phosphorescent light-emitting material. This is because where the triplet energy of the host is lower than the triplet energy of the phosphorescent light-emitting material, the energy may be transferred back from the dopant to the host and the light emission efficiency may decrease. For example, when a phosphorescent light-emitting material having light emission in a visible range is used as a light-emitting dopant, the triplet energy of the host may, in one version, be equal to or higher than 2.0 eV. The values of singlet energy and triplet energy of representative aromatic ring skeletons are shown in Table 1.

TABLE 1

|  | Fluorene | Naphthalene | Anthracene |
|---|---|---|---|
| Molecular weight (g/mol) | 166 | 128 | 178 |
| Singlet energy | 4.1 eV | 4.0 eV | 3.3 eV |
| Triplet energy | 2.9 eV | 2.6 eV | 1.9 eV |

Table 1 demonstrates that when a phosphorescent light-emitting material is used as a light-emitting dopant, the anthracene skeleton may not, in some versions, be suitable as a skeleton of the compound serving as a host because the triplet energy of the anthracene is lower than 2.0 eV. Thus, the number of molecular skeletons that can be employed as hosts corresponding to phosphorescent light-emitting materials may be somewhat limited in some versions, due to restrictions placed on the triplet energy, and thus there may be few materials that are satisfactory.

In one version, the oligofluorene compound in accordance with the present invention is a compound having two or more directly coupled dialkylfluorene skeletons and a naphthalene skeleton with a low molecular weight at at least one end. As shown in Table 1, these two kinds of skeletons have a triplet energy equal to or higher than 2.0 eV. Therefore, they may be suitable for use as skeletons present in a compound serving as a host with respect to a phosphorescent light-emitting dopant.

As described above, the oligofluorene compound in accordance with one embodiment of the present invention has a relatively bulky molecular skeleton and has a relatively low molecular weight. Therefore, this compound has an improved ability to form an amorphous film and a comparatively low vapor deposition temperature. As a result, an amorphous thin film can be obtained that is more stable than that formed from, for example, an oligonaphthalene in which naphthalene is directly coupled in a linear fashion. Further, Table 1 demonstrates that an oligofluorene compound in accordance with an embodiment of the present invention also has a molecular weight lower than that of an oligofluorene in which only dimethylfluorene is directly coupled in a linear fashion. Therefore, the vapor deposition temperature can be decreased. Thus, because the oligofluorene compound in accordance with one embodiment of the present invention has a relatively low singlet energy and a relatively high triplet energy, a high-efficiency organic EL element can be realized in which an increased number of carriers can be injected at a low voltage.

Table 1 also indicates that anthracene has an energy gap of 0.7 eV that is narrower than that of naphthalene. Therefore, the charge injection ability of a compound obtained by introducing an anthracene skeleton can be said to be higher. However, because anthracene also has a relatively low triplet energy (2.0 eV or less), it may be less suitable as a skeleton for a host corresponding to a fluorescent light-emitting material. On the other hand, because naphthalene has a molecular weight lower than that of fluorene and has a relatively low singlet energy of 0.1 eV and a comparatively high triplet energy of 2.6 eV, it may be suitable, and may even be optimally suited, as a skeleton for a host corresponding to a fluorescent light-emitting material. The difference in singlet energy between anthracene and naphthalene is 0.1 eV, and singlet energy between naphthalene and anthracene is 0.7 eV.

As described above, the oligofluorene compound in accordance with aspects of the present invention may satisfy at least one and even all of the above-described requirements (1) to (5), and thus may excel as a host of a light-emitting layer constituting an organic EL element.

Specific examples of the oligofluorene compound in accordance with the present invention are presented below. However, the present invention is not limited thereto.

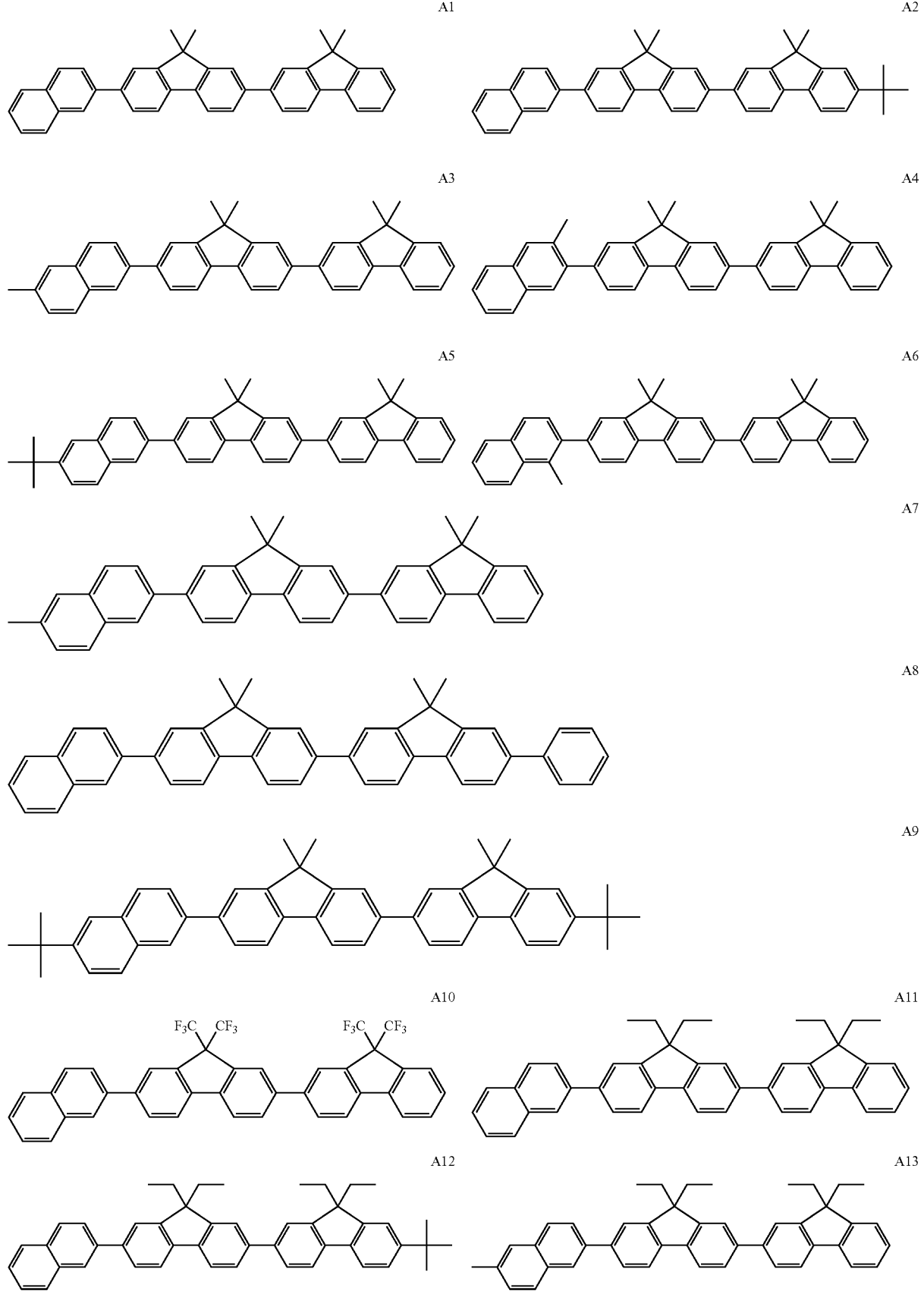

-continued
A14
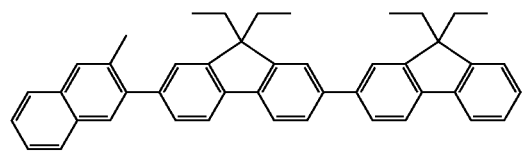
A15
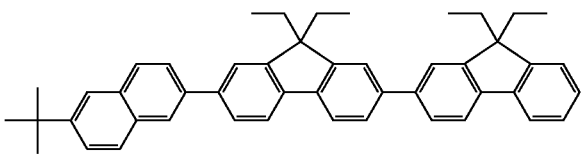
A16
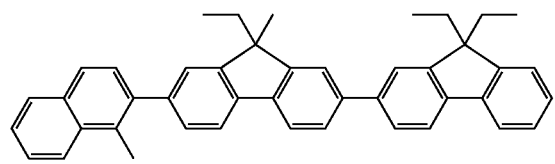
A17
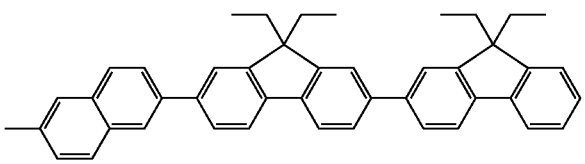
A18
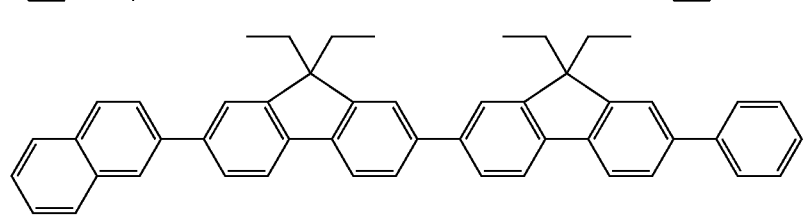
A19
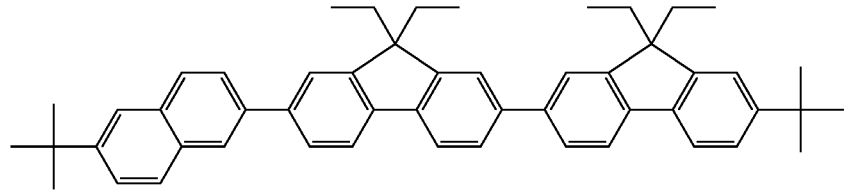
A20
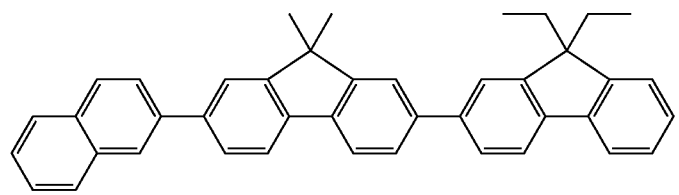
A21
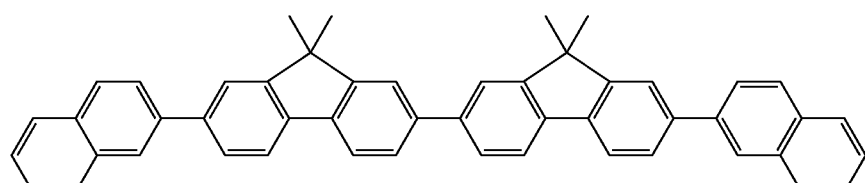
A22
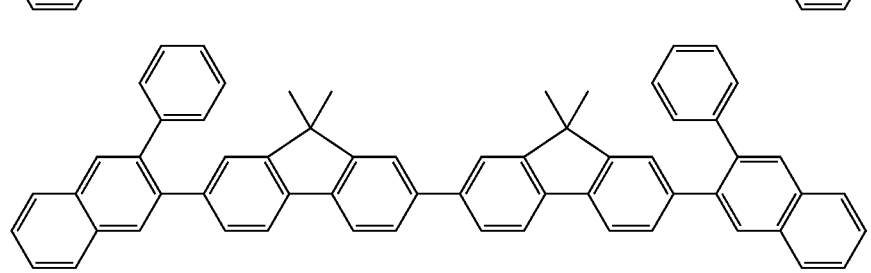
A23
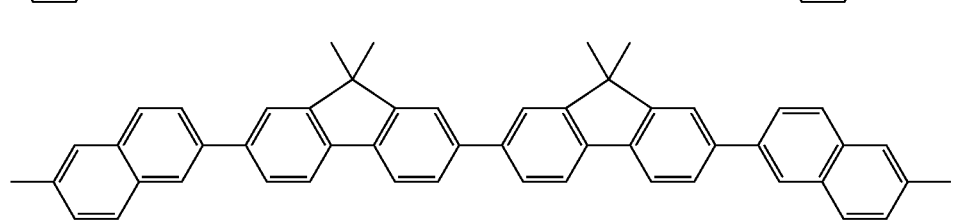

-continued
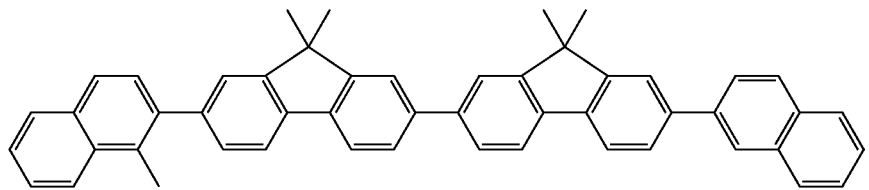
A24
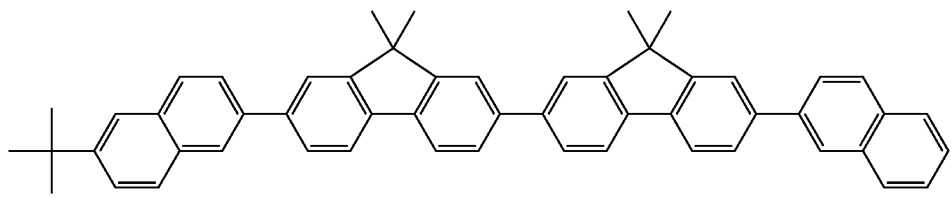
A25
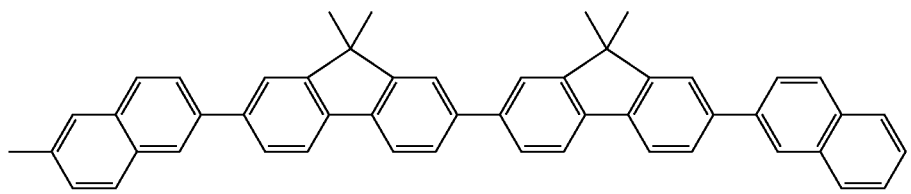
A26
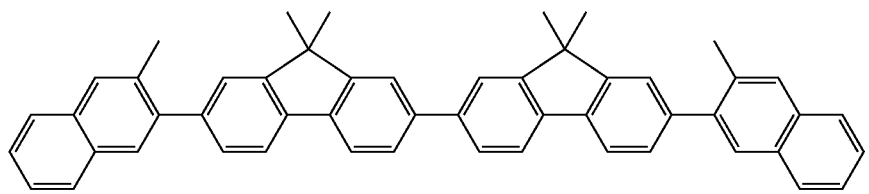
A27
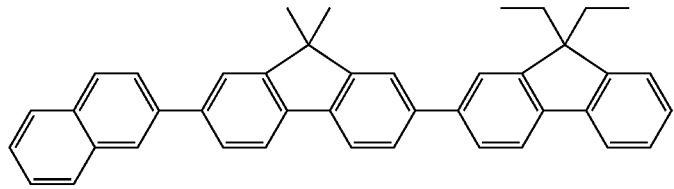
A28
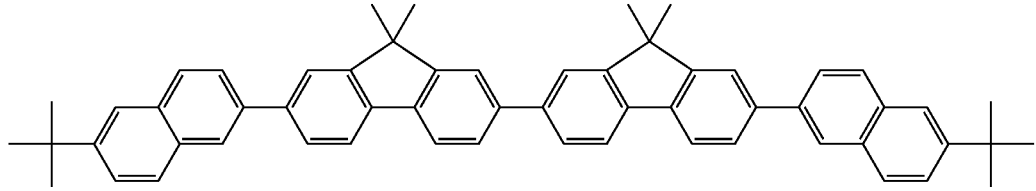
A29
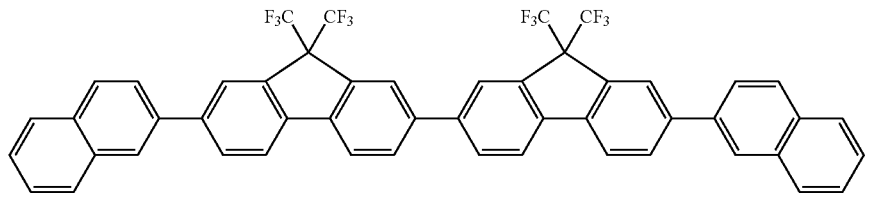
A30
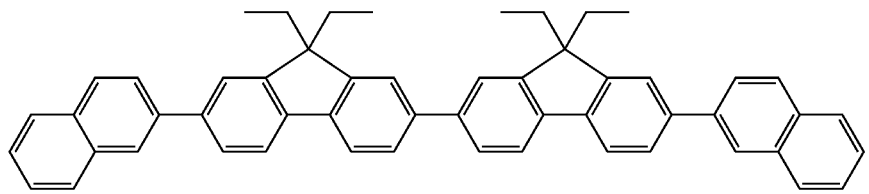
A31

-continued
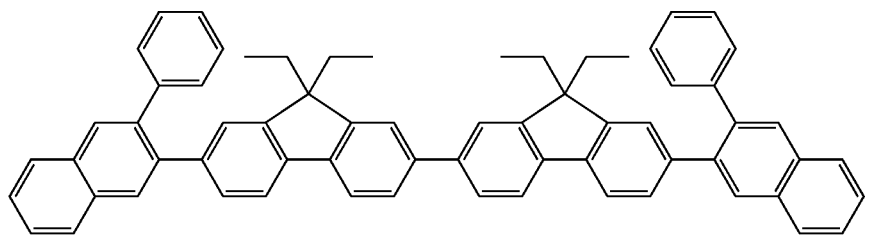
A32
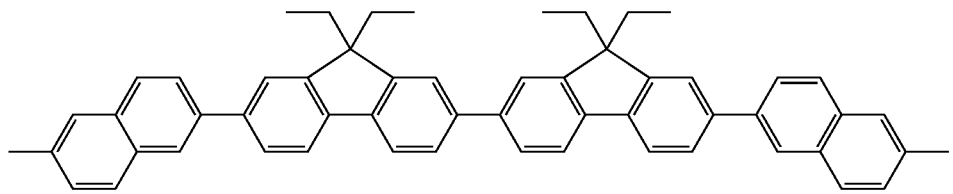
A33
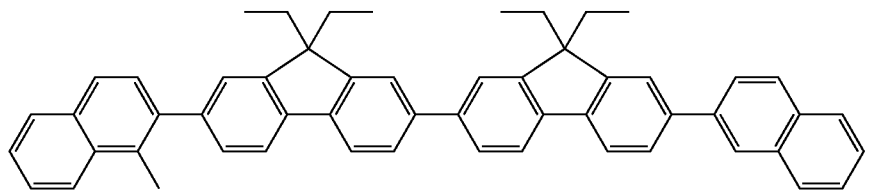
A34
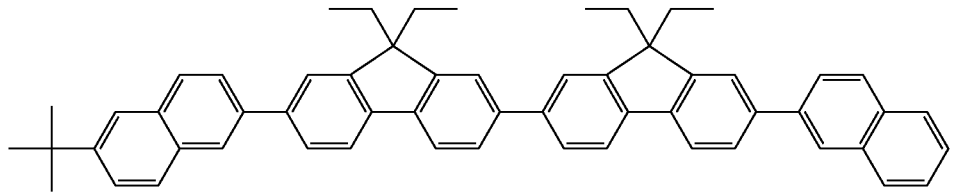
A35
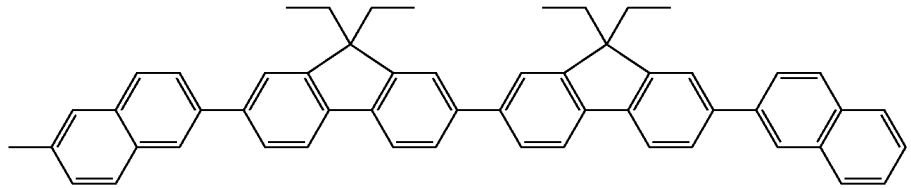
A36
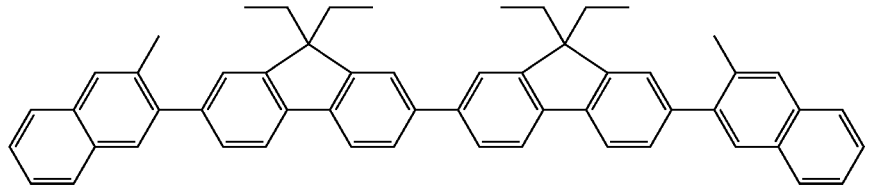
A37
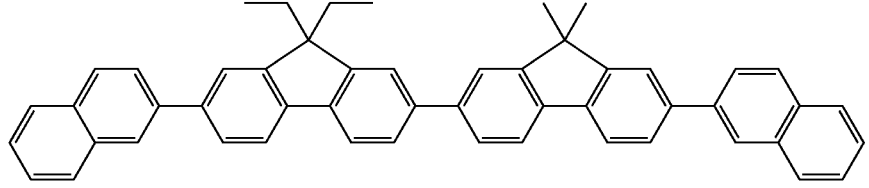
A38
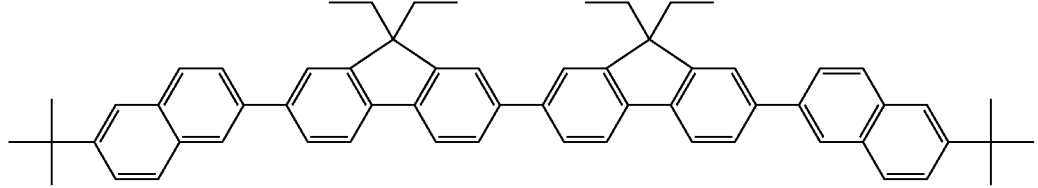
A39

-continued
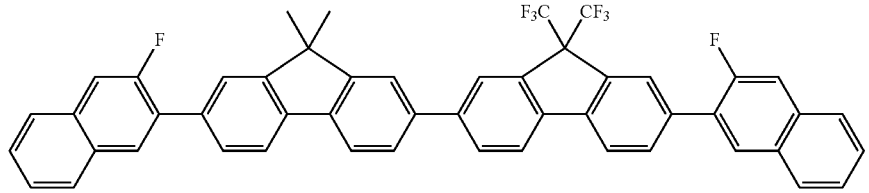
A40
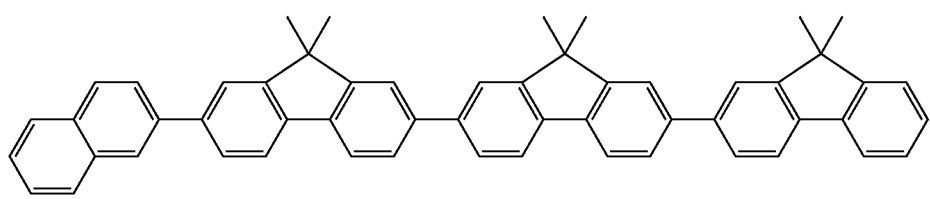
A41
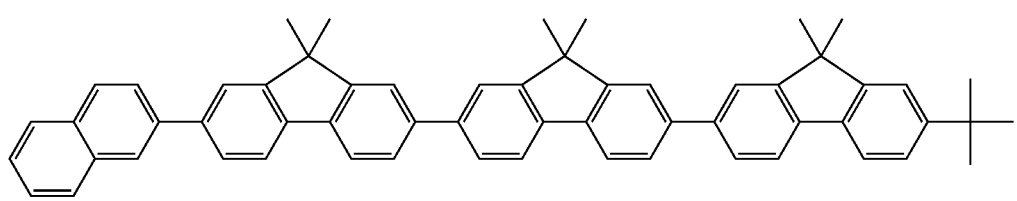
A42
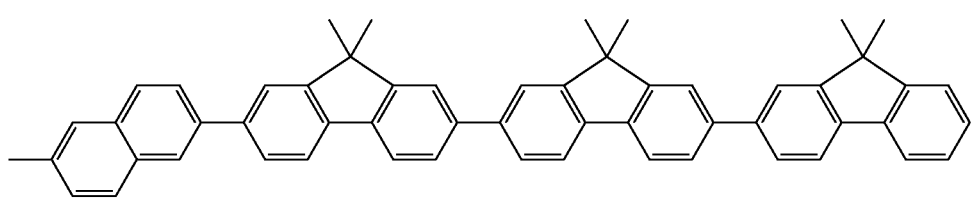
A43
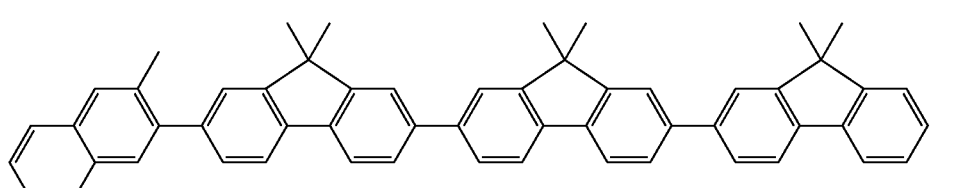
A44
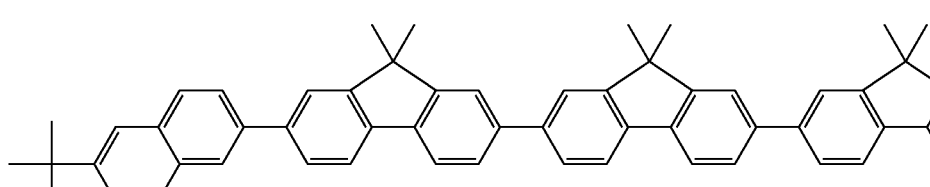
A45
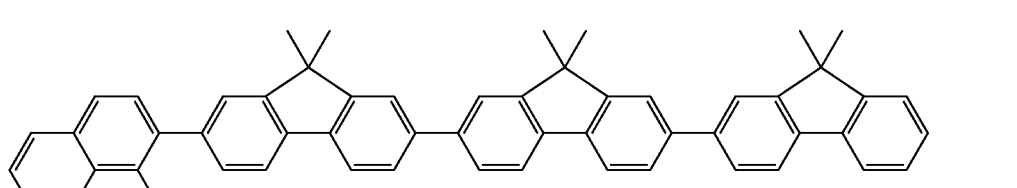
A46
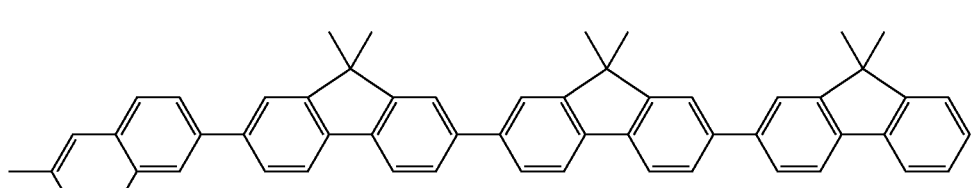
A47

-continued
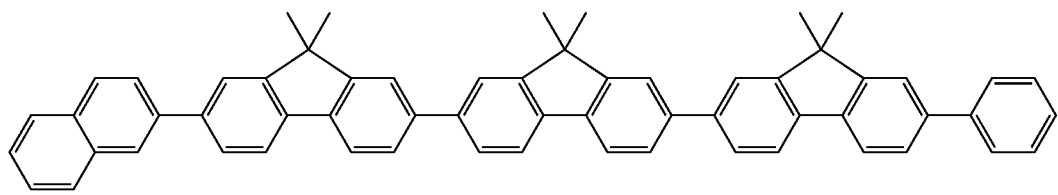
A48
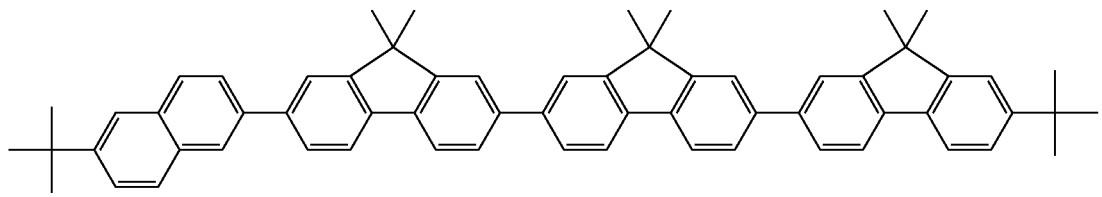
A49
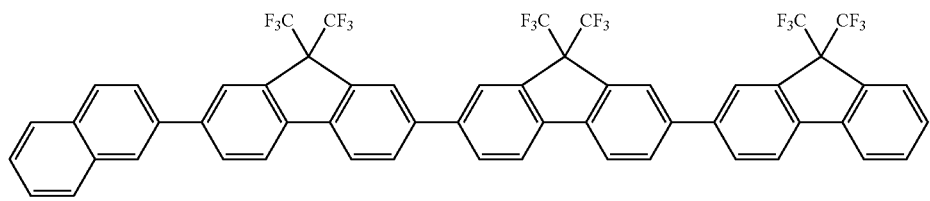
A50
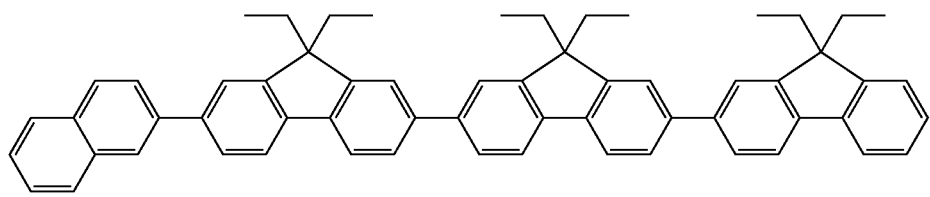
A51
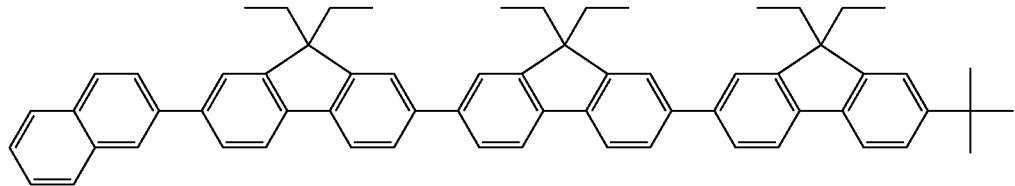
A52
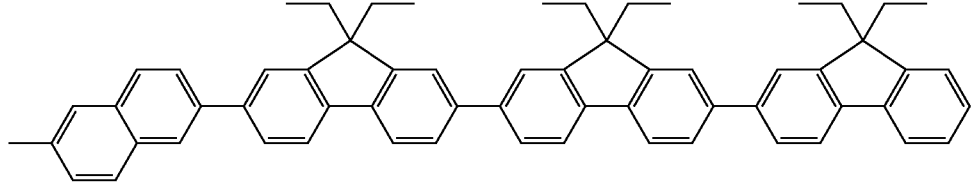
A53
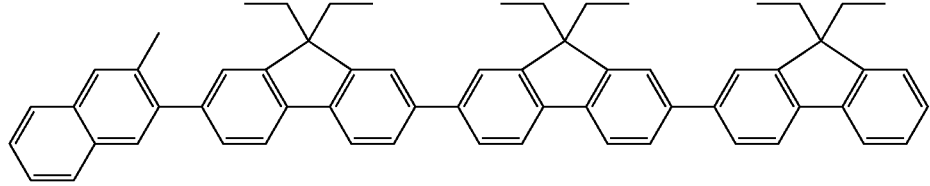
A54
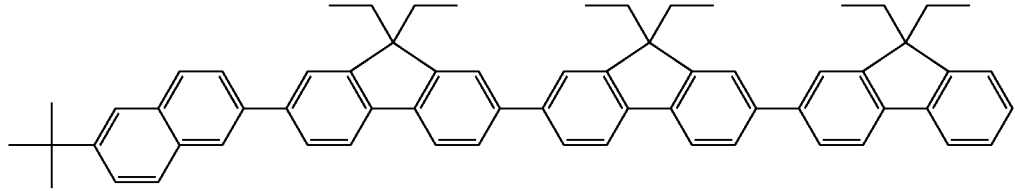
A55

-continued
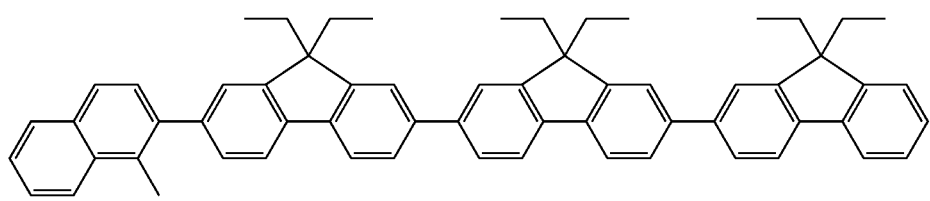
A56
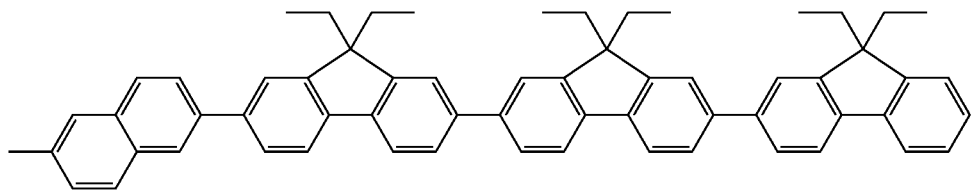
A57
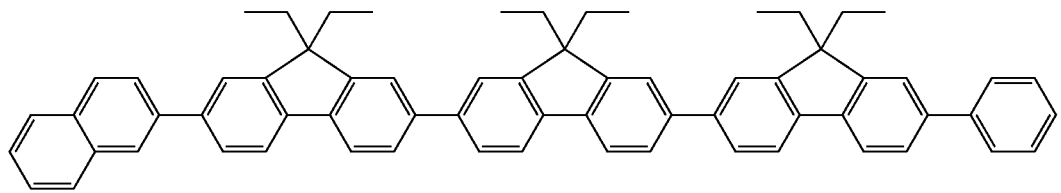
A58
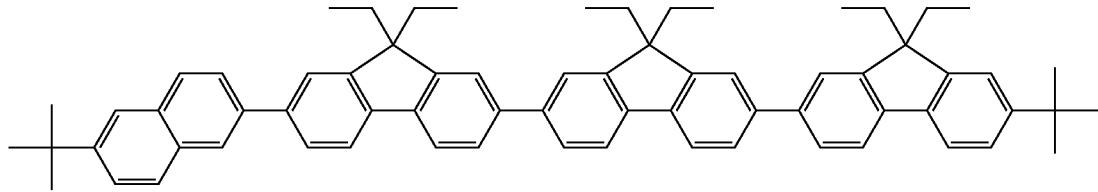
A59
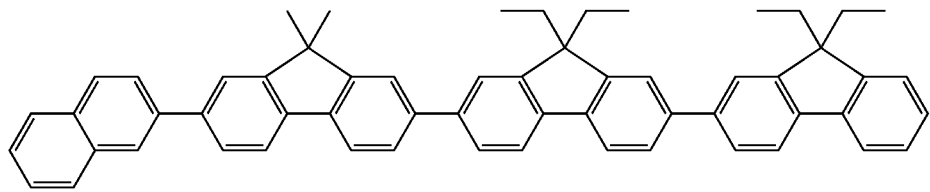
A60
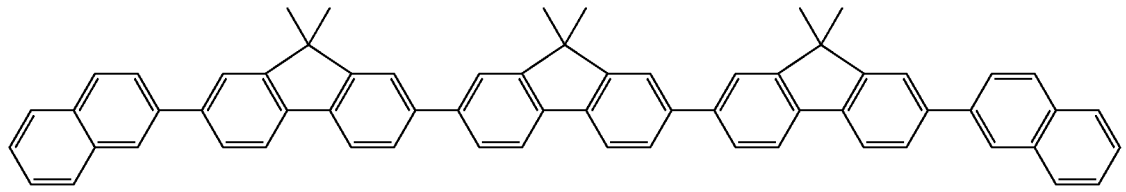
A61
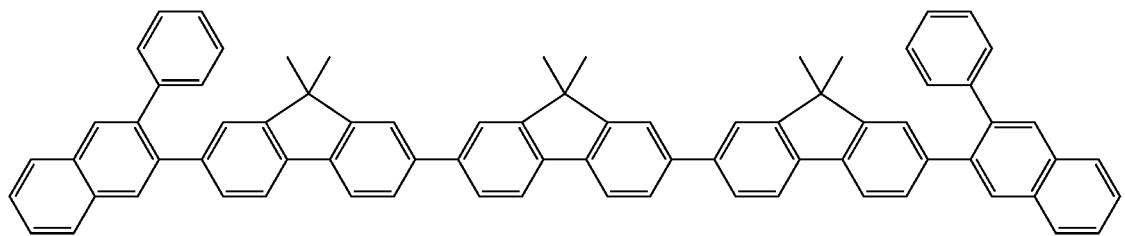
A62
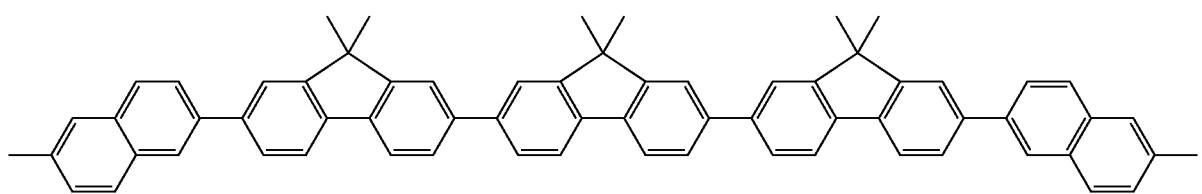
A63

-continued
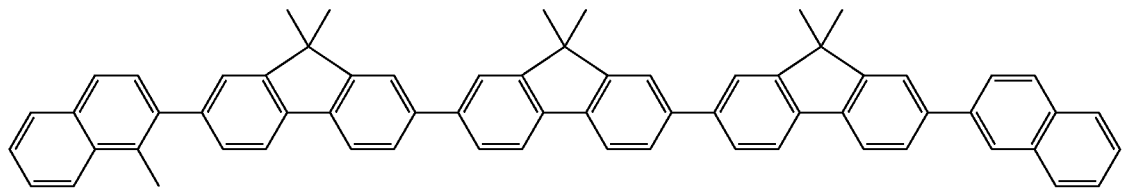
A64
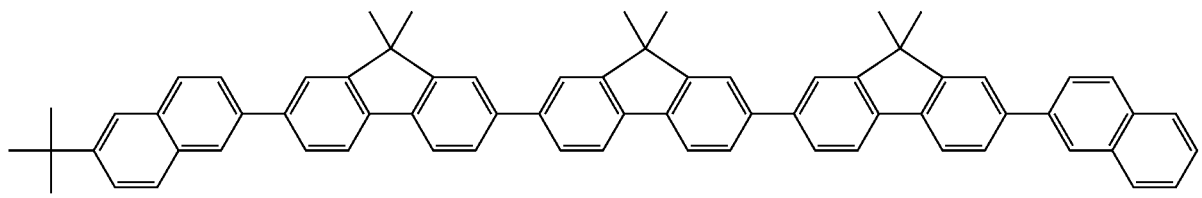
A65
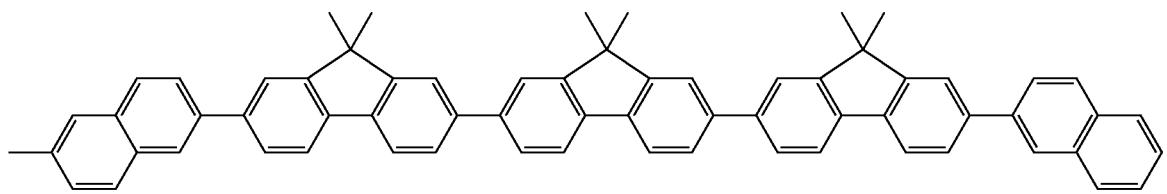
A66
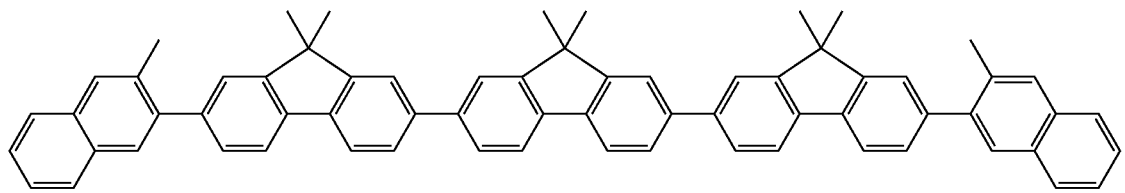
A67
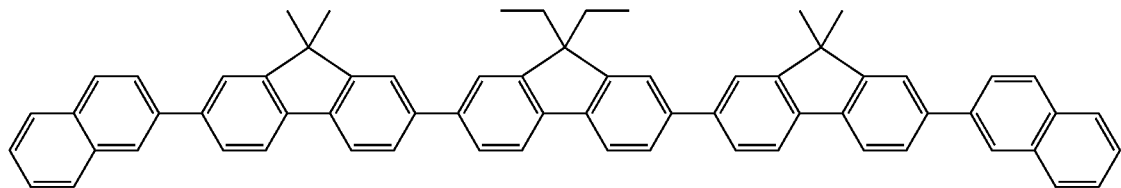
A68
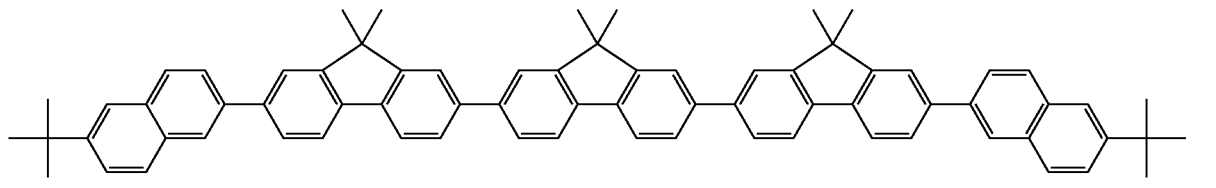
A69
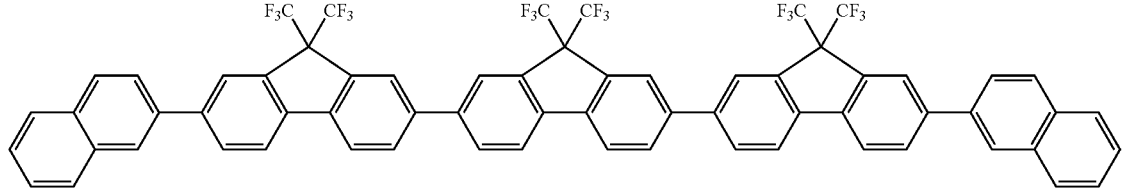
A70
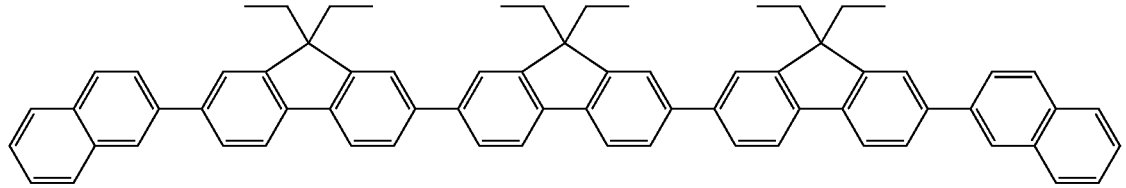
A71

-continued
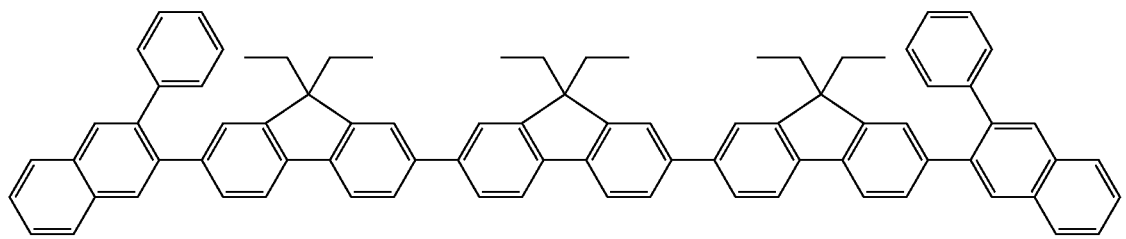
A72
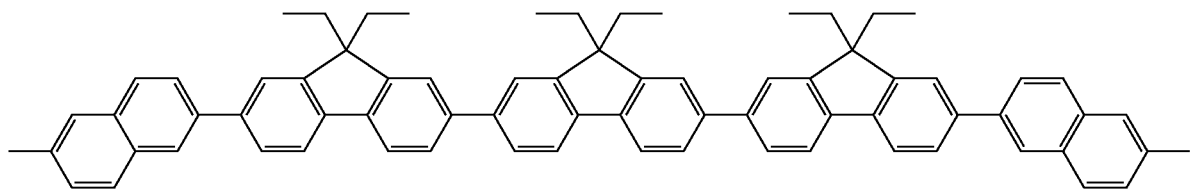
A73
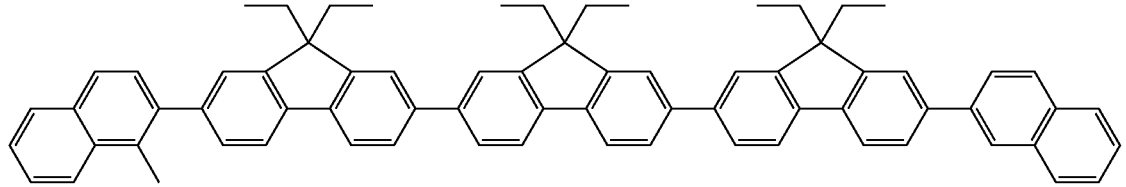
A74
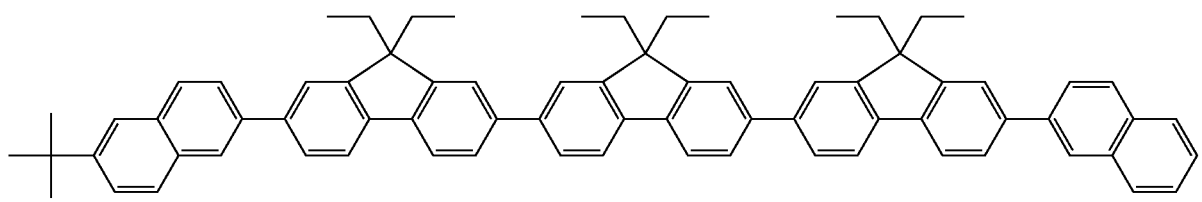
A75
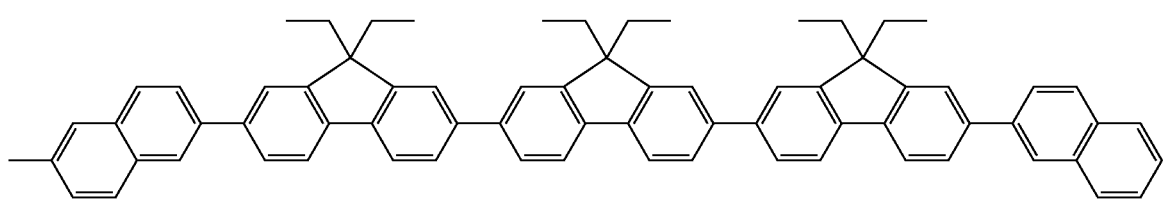
A76
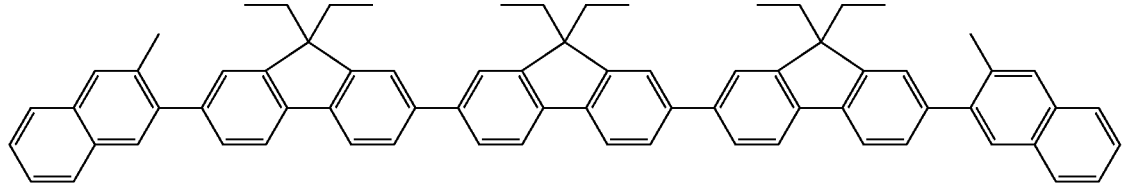
A77
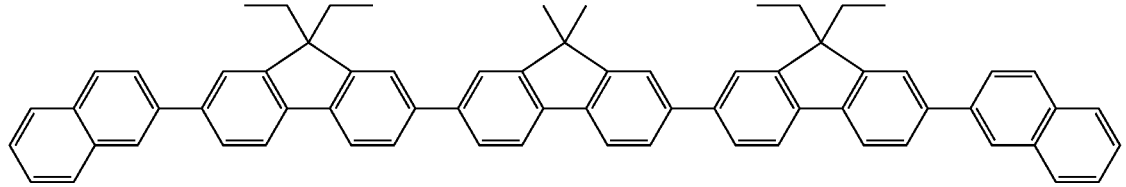
A78

-continued
A79
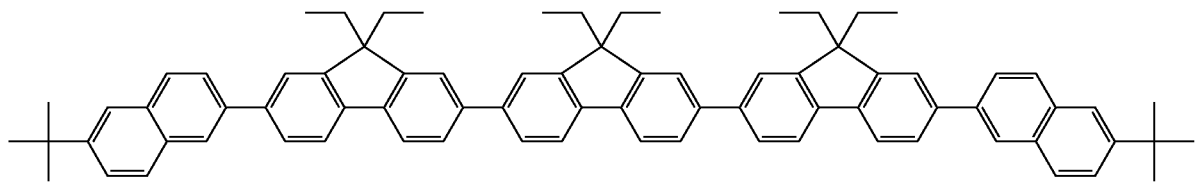
A80
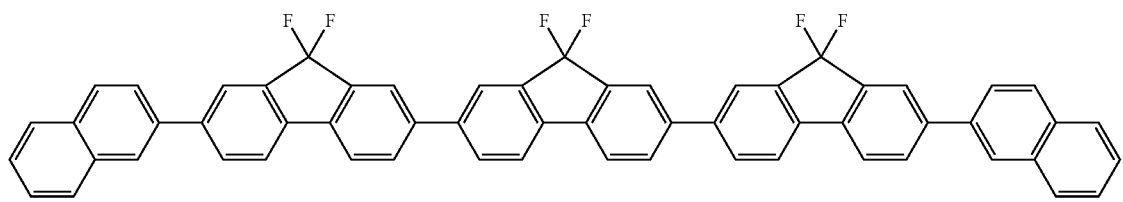
A81
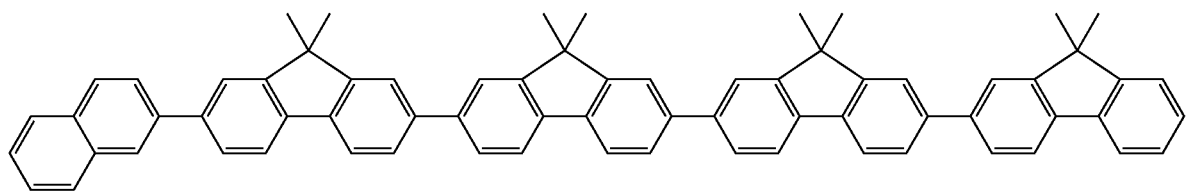
A82
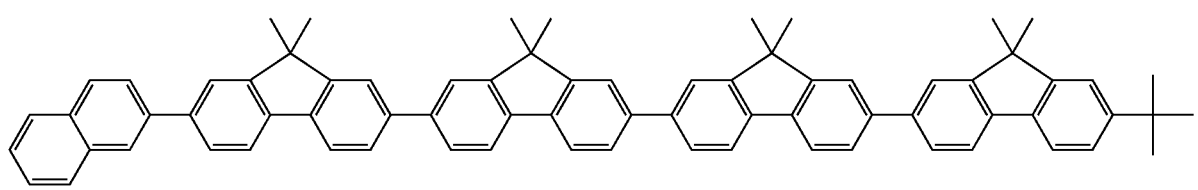
A83
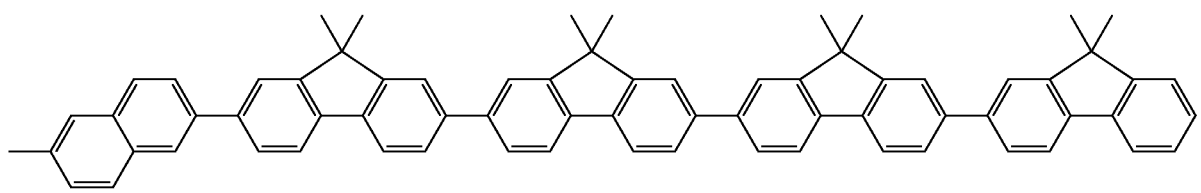
A84
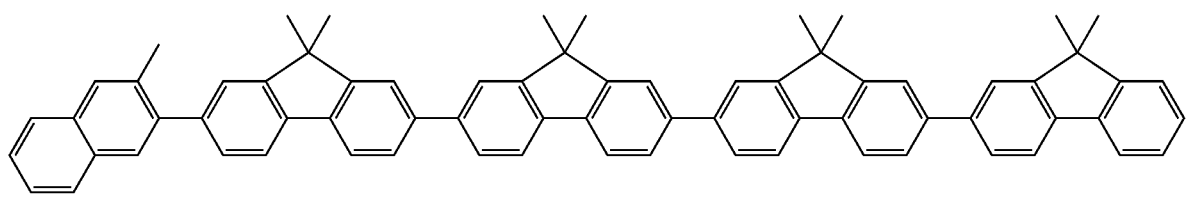
A85
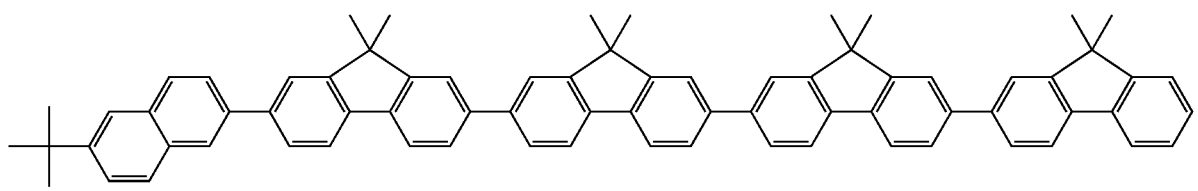

-continued

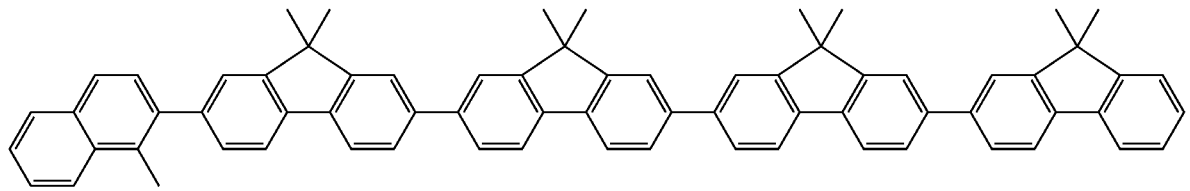

A86

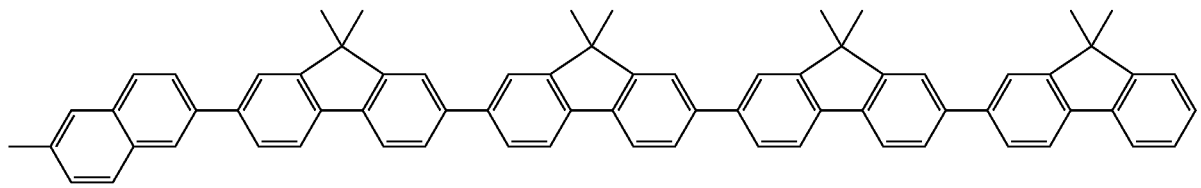

A87

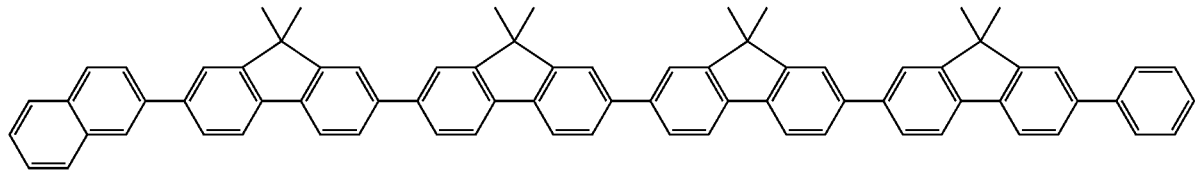

A88

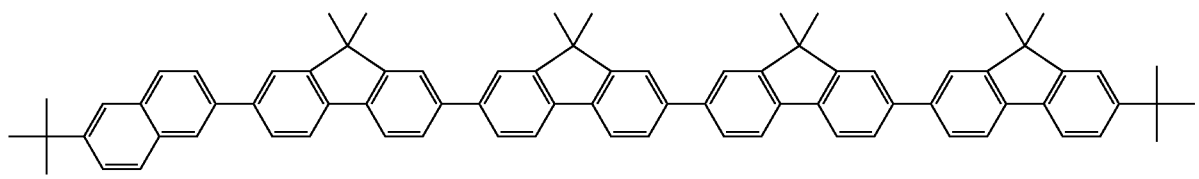

A89

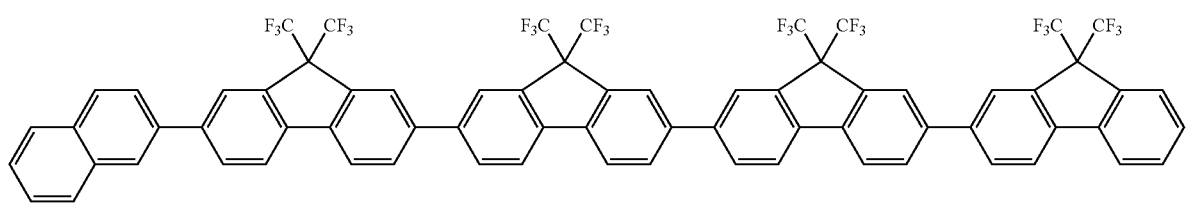

A90

The organic EL element in accordance with the present invention will be described below. The organic EL element in accordance with the present invention is composed of an anode, a cathode, and an organic thin-film layer sandwiched between the anode and the cathode.

The organic EL element in accordance with the present invention will be described below with reference to the appended drawings.

FIG. 1 illustrates an embodiment of the organic EL element in accordance with the present invention. In an organic EL element 1 shown in FIG. 1, a laminated body composed of a metal electrode 11, a metal electrode layer 12, an electron transport layer 13, a light-emitting layer 14, a hole transport layer 15, and a transparent electrode 16, disposed in the order of description from above, is provided on a transparent substrate 17. In the organic EL element 1 shown in FIG. 1, the organic thin-film layer is a laminated body composed of three layers: electron transport layer 13, light-emitting layer 14, and hole transport layer 15.

In the organic EL element in accordance with the present invention, the oligofluorene compound in accordance with the present invention is contained in the organic thin-film layer. In the organic EL element shown in FIG. 1, any of the electron transport layer 13, light-emitting layer 14, and hole transport layer 15 can contain the oligofluorene compound in accordance with the present invention.

The organic EL element in accordance with the present invention can be employed in any one or more of the below-described embodiments thereof:

(i) Anode/Light-emitting layer/Cathode.
(ii) Anode/Hole transport layer/Light-emitting layer/Cathode.
(iii) Anode/Light-emitting layer/Electron transport layer/Cathode.
(iv) Anode/Hole transport layer/Light-emitting layer/Electron transport layer/Cathode (FIG. 1).
(v) Anode/Hole transport layer/Electron-exciton blocking layer/Light-emitting layer/Electron transport layer/Cathode.
(vi) Anode/Hole transport layer/Light-emitting layer/Hole-exciton blocking layer/Electron transport layer/Cathode.
(vii) Anode/Hole transport layer/Electron-exciton blocking layer/Light-emitting layer/Hole-exciton blocking layer/Electron transport layer/Cathode.

The oligofluorene compound in accordance with the present invention can be used in any one or more of the above-described embodiments (i) to (vii).

However, these embodiments are intended merely to illustrate examples of specific configurations of the organic EL element, and thus the configuration of the organic EL element in accordance with the present invention is not limited thereto. For example, a charge injection layer may be provided between the electrodes and charge transport layers, and an adhesive layer may be provided to increase adhesivity of the film. As a further example, an interference layer may be provided to efficiently take out the emission generated in the light-emitting layer.

In one version of the organic EL element in accordance with the present invention, the organic thin-film layer contains a light-emitting layer, this light-emitting layer comprises both a host and a guest, the host is an oligofluorene compound in accordance with the present invention, and the guest is a phosphorescent light-emitting dopant. In another version of the organic EL element in accordance with the present invention, the guest may comprise a plurality of phosphorescent light-emitting dopant, such as two or three kinds of dopant.

In one embodiment, the phosphorescent light-emitting dopant as referred to herein is an organometallic complex, such as a compound represented by a General Formula (3) below.

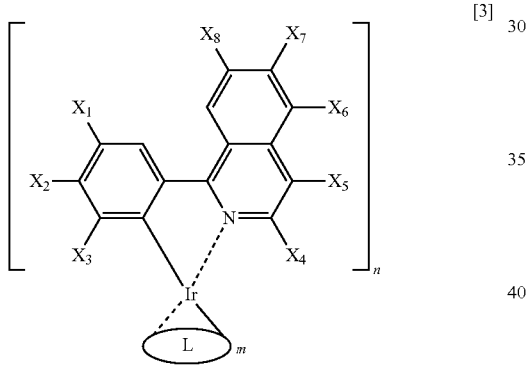

[3]

In Formula (3), $X_1$ to $X_8$ each represent a hydrogen atom, an alkyl group, a halogen atom, or an alkoxy group.

Examples of the alkyl group represented by $X_1$ to $X_8$ may include, but are not limited to, a methyl group, a trifluoromethyl group, an ethyl group, an n-propyl group, an isopropyl group, an n-butyl group, and a tertiary butyl group.

Examples of the halogen atom represented by $X_1$ to $X_8$ may include, but are not limited to, fluorine, chlorine, bromine, and iodine.

Examples of the alkoxy group represented by $X_1$ to $X_8$ may include, but are not limited to, a methoxy group and an ethoxy group.

In Formula (3), n is 2 or 3, such as 3.
In Formula (3), m is 0 or 1, such as 0.
In Formula (3), L is a ligand represented by a General Formula (4) or (5) below.

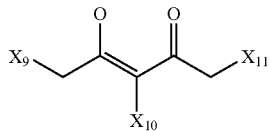

[4]

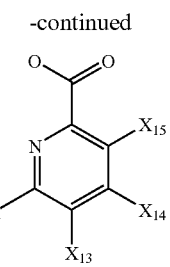

[5]

In Formulas (4) and (5), $X_9$ to $X_{15}$ each represent a hydrogen atom, an alkyl group, a halogen atom, and an alkoxy group.

Specific examples of the alkyl group, halogen atom, and alkoxy group represented by $X_9$ to $X_{15}$ are identical to those of $X_1$ to $X_8$ described above.

In another embodiment, the phosphorescent light-emitting dopant is a compound represented by a General Formula (6) below.

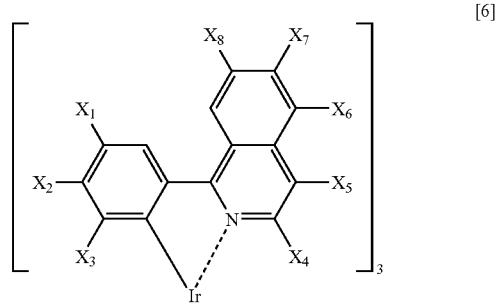

[6]

In Formula (6), $X_1$ to $X_8$ each represent a hydrogen atom, an alkyl group, a halogen atom, or an alkoxy group. Specific examples of the alkyl group, halogen atom, and alkoxy group represented by $X_1$ to $X_8$ are identical to those of $X_1$ to $X_8$ in Formula (3) described above.

In one version, the phosphorescent light-emitting dopant may be a compound represented by a General Formula (7) or (8) below.

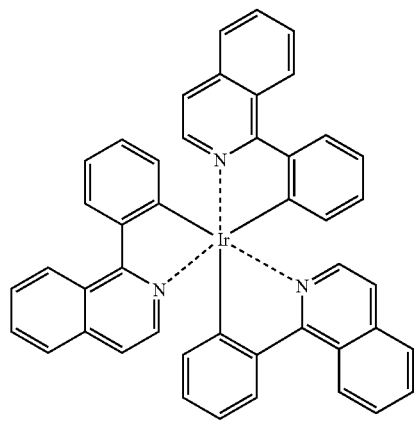

[7]

-continued
[8]
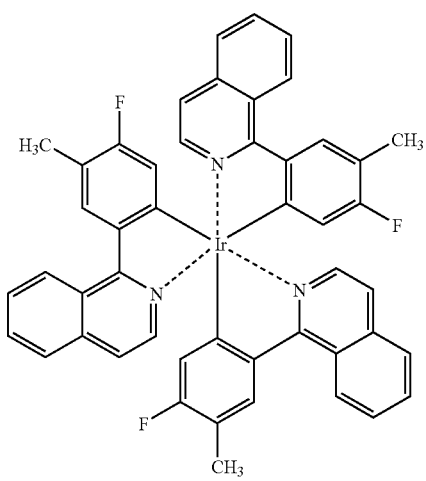
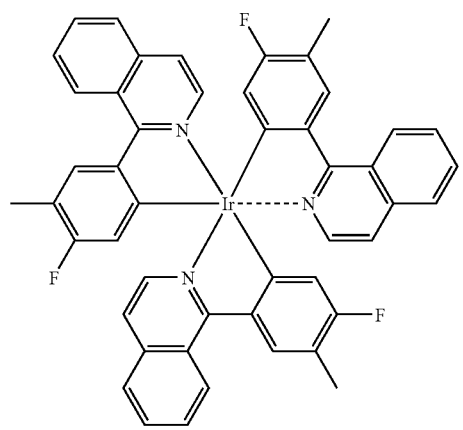
Specific examples of the compounds serving as the phosphorescent light-emitting dopant are shown below. However, the present invention is not limited thereto.
X1
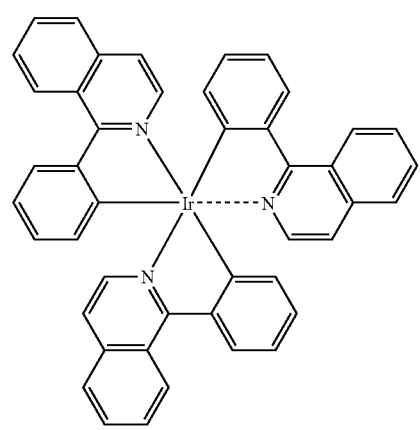
X4
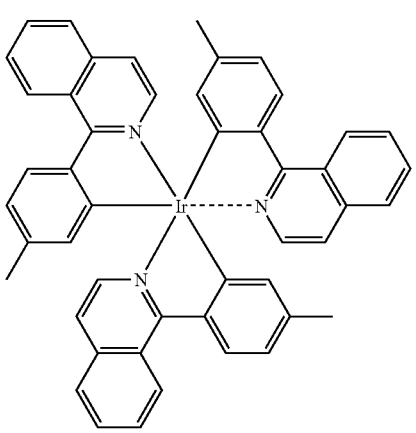
X2
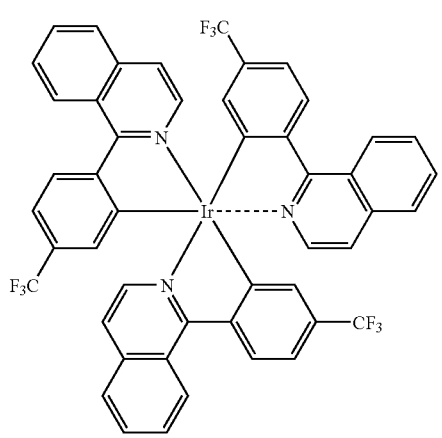
X5
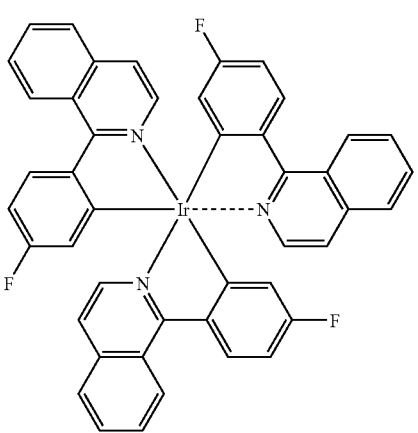

35
-continued
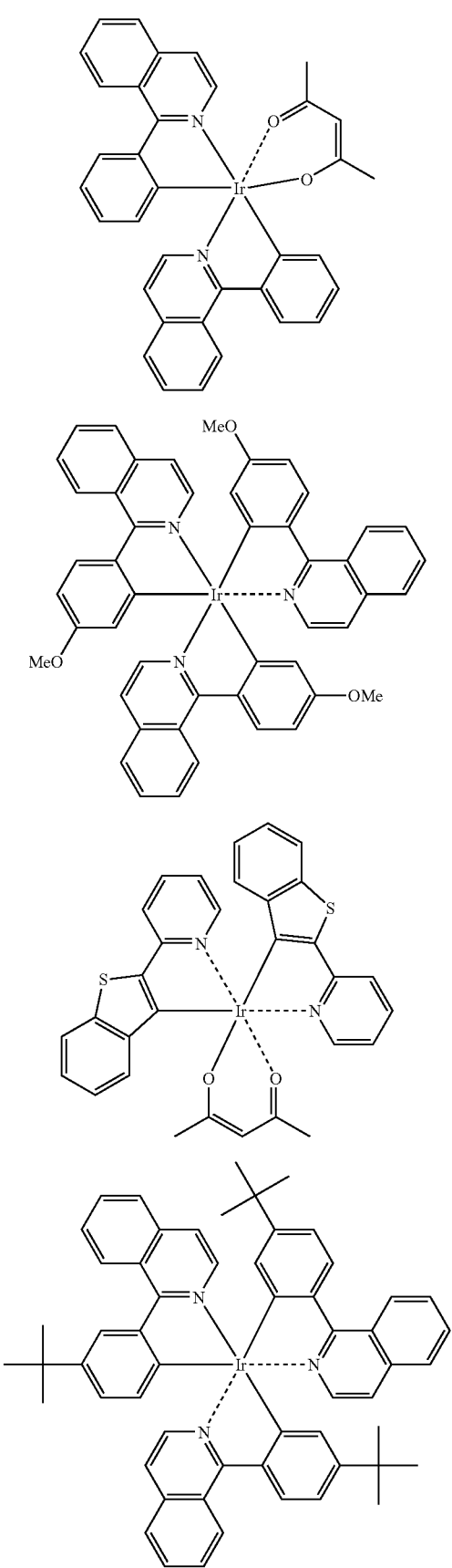
X6
X7
X8
X9
36
-continued
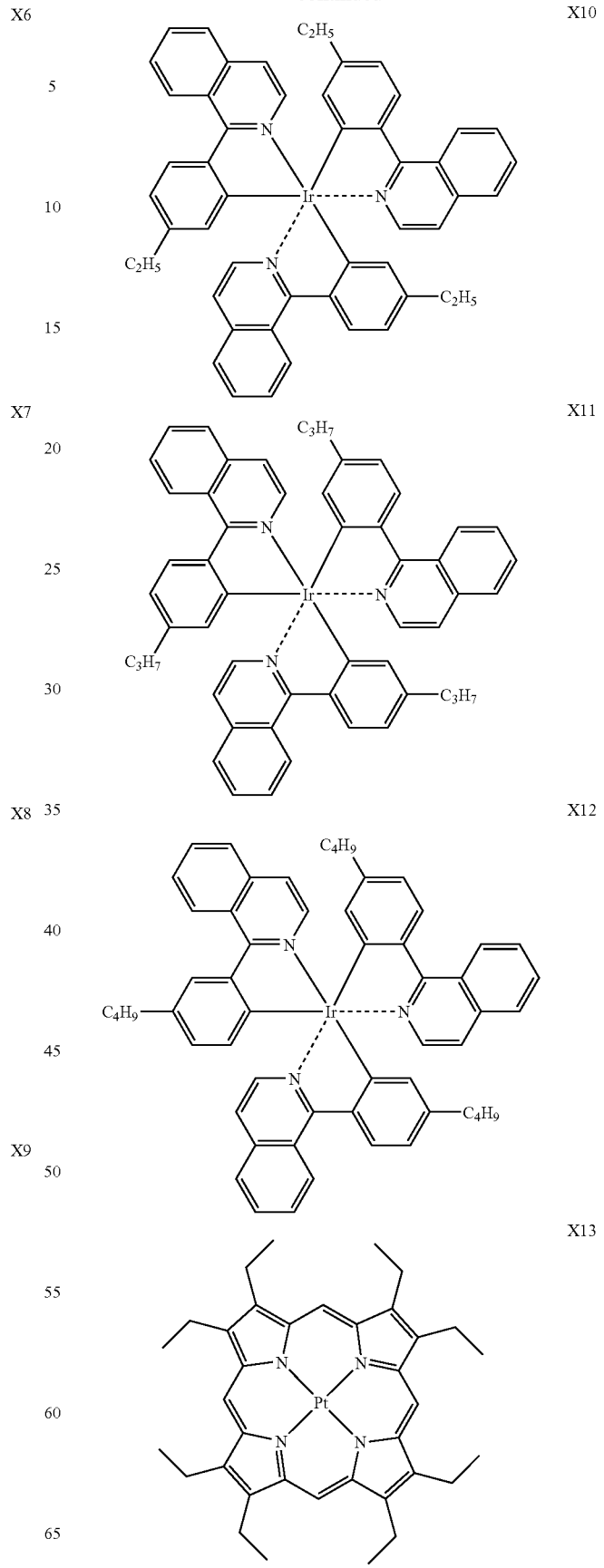
X10
X11
X12
X13

X14 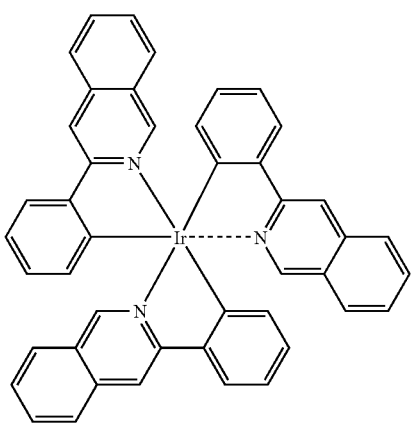

X17 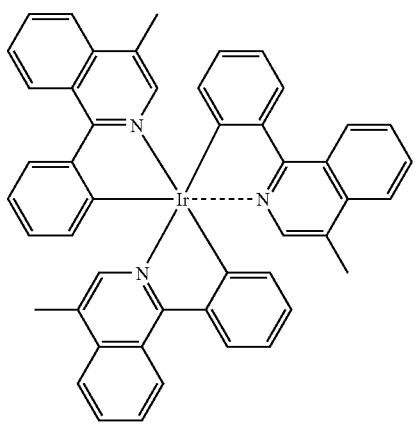

X15 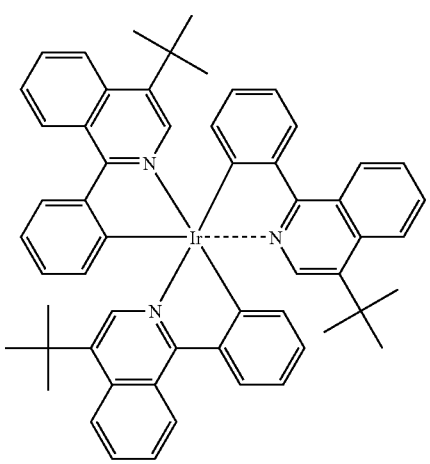

X16

As described hereinabove, in one version the organic EL element in accordance with the present invention uses the oligofluorene compound as a host contained in a light-emitting layer. Since the oligofluorene compound in accordance with the present invention has a sufficiently high triplet excitation energy, where a guest contained in the light-emitting layer (light-emitting dopant) is a phosphorescent light-emitting material, the organic EL element in accordance with the present invention is capable of demonstrating a remarkable effect. When the light-emitting layer that makes up a portion of the organic EL element is composed of a host and a guest with a carrier transport ability, the process leading to light emission may be a combination of the following several processes.

1. Transport of electrons and holes on a host.
2. Transport of electrons and holes on a guest.
3. Exciton generation on a host.
4. Exciton generation on a guest.
5. Energy transfer between host molecules.
6. Energy transfer from a host molecule to a guest molecule.

Where the guest is a phosphorescent light-emitting material, both the singlet excitons and triplet excitons can contribute to light emission. The singlet excitons and triplet excitons may appear during the competition of various decay processes.

In order to increase light emission efficiency of an organic EL element, a good balance of carriers (holes and electrons) injected from the electrodes may be required. Furthermore, it may be necessary that a large amount of carriers be injected into the light-emitting layer and that excitons be generated with relatively good efficiency. Because the oligofluorene compound in accordance with the present invention has a sufficiently narrow energy gap, the excitons can be generated with good efficiency due to the aforementioned carrier confinement effect. Furthermore, because the generated excitons are generally localized within the light-emitting layer, energy can be relatively easily transferred to the guest molecule, and light emission efficiency may be increased.

In one embodiment, the organic light-emitting element in accordance with the present invention uses the oligofluorene compound and a phosphorescent light-emitting dopant as constituent materials of the light-emitting layer, but other materials may be also added thereto. For example, a material enhancing or inhibiting hole transport ability may be added, and a material enhancing or inhibiting electron transport ability may be added. Furthermore, a material that can cause efficient energy transfer of excitons located in the light-emitting layer to the light-emitting dopant may be added (see Japanese Patent Laid-Open No. 2006-128632). Names and molecular formulas of compounds that are generally suitable as a constituent material of organic light-emitting elements are shown below.

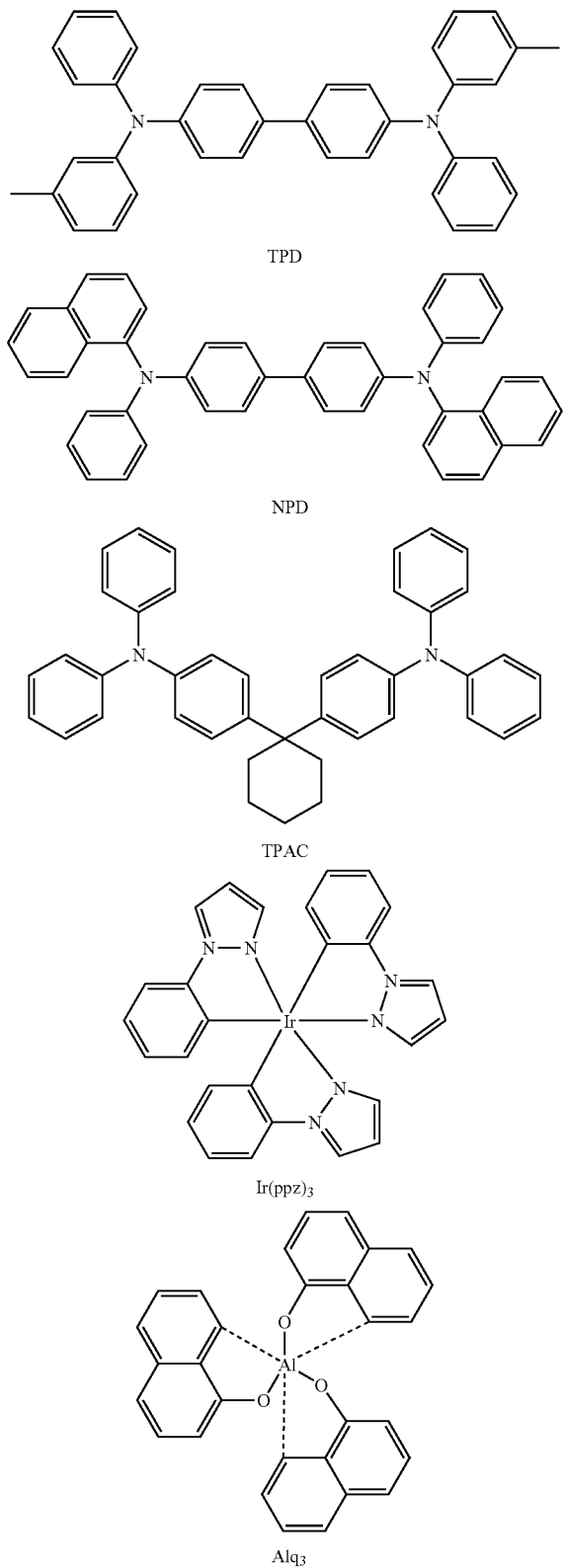

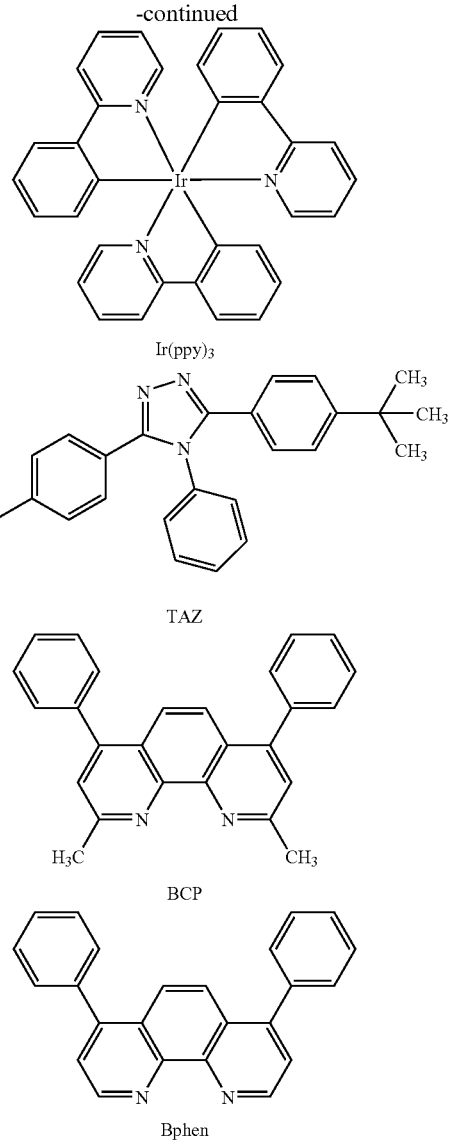

Specific examples of materials enhancing the hole transport ability may include, but are not limited to, TPD, NPD, and TPAC.

Specific examples of materials inhibiting the hole transport ability may include, but are not limited to, BCP and Bphen.

Specific examples of materials enhancing the electron transport ability may include, but are not limited to, TAZ, BCP, $Alq_3$, and Bphen.

$Ir(ppz)_3$ is a specific example of material inhibiting the electron transport ability.

$Ir(ppy)_3$ is a specific example of material that can cause efficient energy transfer of excitons located in the light-emitting layer to the light-emitting dopant.

Specific examples of materials used to form the anode can include, but are not limited to, ITO and IZO.

Specific examples of materials used to form the cathode can include, but are not limited to, aluminum, lithium, silver, IZO, and chromium.

A substrate used in the organic EL element in accordance with the present invention is not particularly limited, and non-transparent substrates such as metal substrates and ceramic substrates or transparent substrates such glass, quartz, and plastic sheet can be used. The light emission color can be controlled by using a color filter film, a color conversion filter film, a dielectric reflective film, or, the like, on the substrate. The element can be also fabricated by producing a thin-film transistor on the substrate and connecting thereto. As for the direction of emission of light from the element, the element can be any one of a bottom emission type in which the light is taken out from one substrate side, and a top emission type in which the light is taken out from the opposite side.

EXAMPLES

The present invention will be specifically described below with reference to the Examples, but the present invention is not limited thereto.

Example 1

Synthesis of Example Compound No. A21

Toluene: 20 mL.

Ethanol: 10 mL.

2M-Aqueous solution of sodium carbonate: 20 mL.

The reaction solution was then stirred for 7 h at 80° C. under a nitrogen flow. Upon completion of the reaction, the reaction solution was filtered, and the filtered-out crystals were washed successively with water and ethanol and then dissolved in chlorobenzene. The solution was filtered with silica gel under heating and recrystallization was carried out with a chlorobenzene solution to obtain a crude product, 1.60 g, of Example Compound No. A21. The yield was 80.0%.

The crude product was sublimation purified. A thin film was then formed by vapor co-depositing the purified product of Example Compound No. A21 and Ir(ppy)$_3$, which is a sensitizer, at a weight mixing ratio of 75:25. A phosphorescence spectrum of the formed thin film was measured with a fluorescence spectrometer (trade name: HITACHI-F4500). A triplet excitation energy of the Example Compound No. A21 was then found from the phosphorescence spectrum obtained. The result was 2.16 eV.

An absorption spectrum of the thin film obtained by vapor depositing the Example Compound No. A21 alone was measured using a UV-visible absorption spectrometer (trade

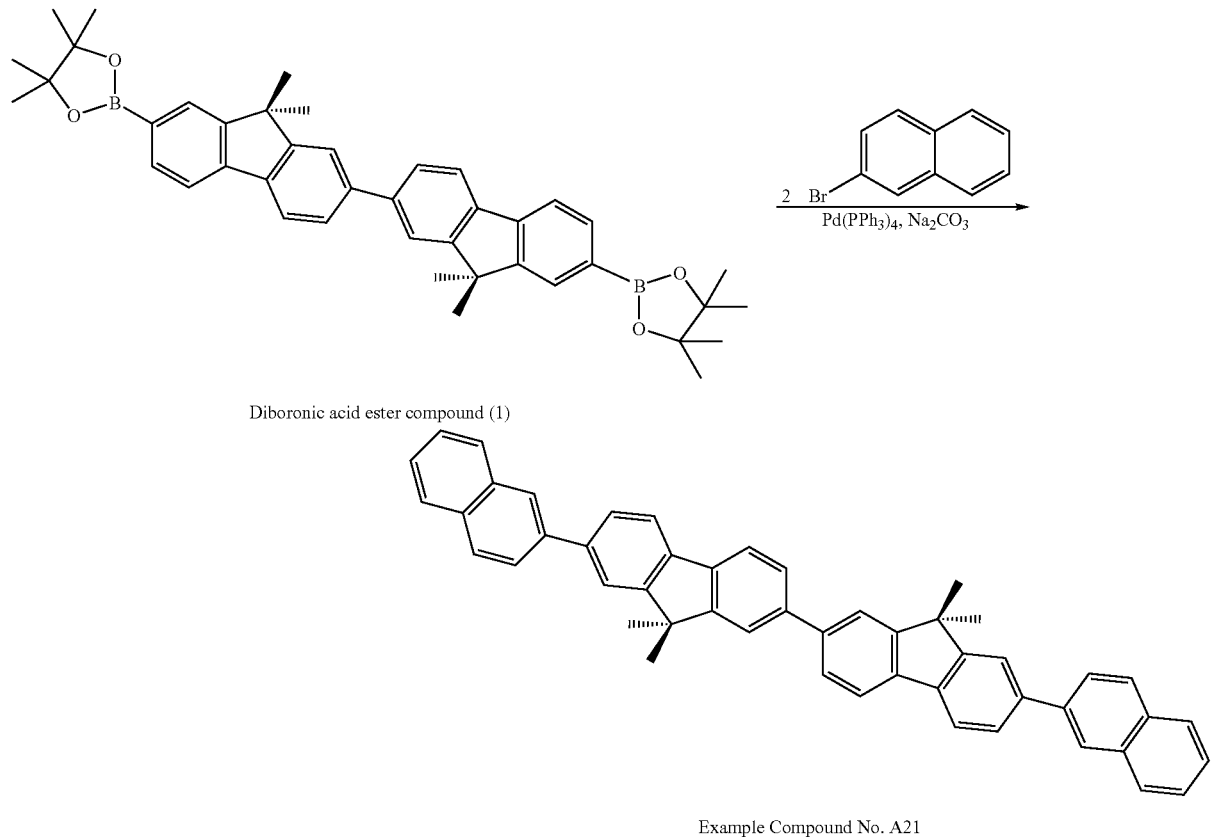

Diboronic acid ester compound (1)

Example Compound No. A21

The following reagents and solvents were charged into a pear-shaped flask with a capacity of 300 mL.

Diboronic acid ester compound (1): 2.0 g (3.13 mmol).

2-Bromonaphthalene: 1.62 g (7.83 mmol).

Pd(PPh$_3$)$_4$: 0.2 g.

name: JASCO-V580). An energy gap was found from the ends of the absorption spectrum obtained. The result was 2.99 eV.

A glass transition temperature of the Example Compound No. A21 was measured with a DSC (Differential Scanning Calorimeter). The result was 180° C.

Example 2

Synthesis of Example Compound No. A61

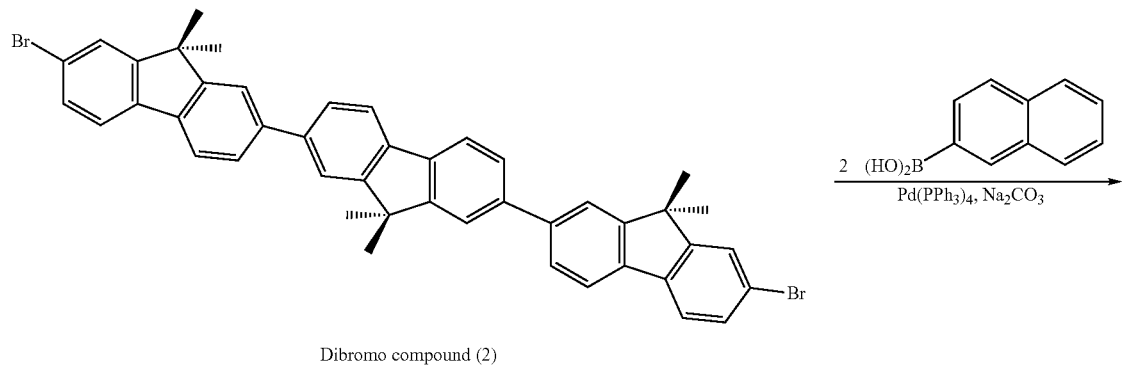

Dibromo compound (2)

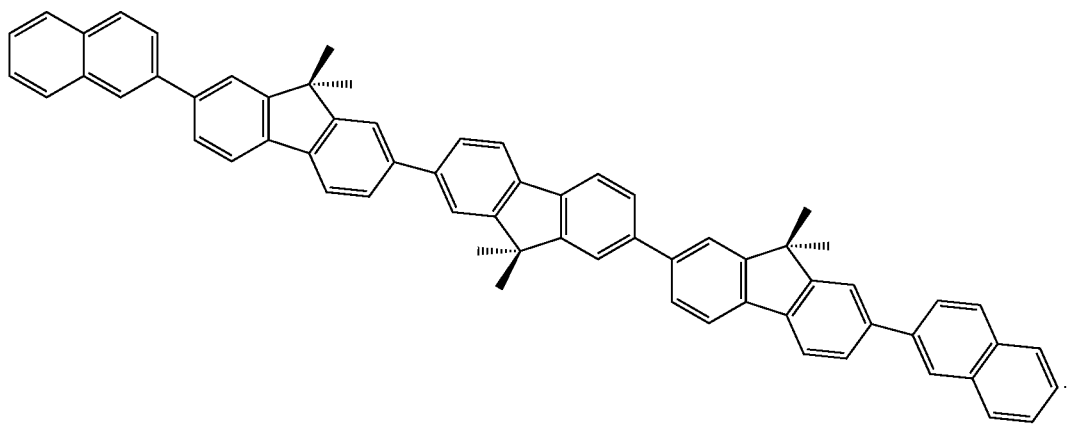

Example Compound No. A61

The following reagents and solvents were charged into a pear-shaped flask with a capacity of 300 mL.
Dibromo compound (2): 1.5 g (2.04 mmol).
2-Naphthylboronic acid: 0.876 g (5.09 mmol).
Pd(PPh$_3$)$_4$: 0.2 g.
Toluene: 40 mL.
Ethanol: 20 mL.
2M-Aqueous solution of sodium carbonate: 40 mL.

The reaction solution was then stirred for 10 h at 80° C. under a nitrogen flow. Upon completion of the reaction, the reaction solution was filtered. The crystals obtained were washed successively with water and ethanol and then dissolved in chlorobenzene. The solution was filtered with silica gel under heating and recrystallization was carried out with a mixed solution of chloroform and ethanol to obtain a crude product, 1.60 g, of Example Compound No. A61. The yield was 78.3%.

The crude product was sublimation purified. A thin film was then formed by vapor co-depositing the purified product of Example Compound No. A61 and Ir(ppy)$_3$, which is a sensitizer, at a weight mixing ratio of 75:25. A phosphorescence spectrum of the formed thin film was then measured and a triplet excitation energy was found in the same manner as in Example 1. The result is shown in Table 3.

An absorption spectrum of the thin film obtained by vapor depositing the Example Compound No. A61 alone was measured in the same manner as in Example 1 and an energy gap was found in the same manner as in Example 1. The result is shown in Table 3.

A glass transition temperature of the Example Compound No. A61 was measured in the same manner as in Example 1 by using a DSC. The result is shown in Table 3.

The oligofluorene compounds shown in Table 2 below can be synthesized by using the halogen modifications and boronic acid derivatives shown in Table 2 and employing any of the first through third synthesis methods.

TABLE 2

| Oligofluorene Compound | Halogen modification | Boronic acid derivative 1 | Boronic acid derivative 2 | Synthesis method[Note 1] |
|---|---|---|---|---|
| Example Compound No. A22 | 2,7-dibromo bis(9,9-dimethylfluorene) structure (Br on each terminal fluorene) | 2-phenylnaphthalene-B(OH)$_2$ | 2-phenylnaphthalene-B(OH)$_2$ | First synthesis method |
| Example Compound No. A2 | 2-bromo-7-tert-butyl bis(9,9-dimethylfluorene) structure | 2-naphthyl-B(OH)$_2$ | None | Third synthesis method |
| Example Compound No. A30 | 2,7-dibromo bis(9,9-bis(trifluoromethyl)fluorene) structure | 2-naphthyl-B(OH)$_2$ | 2-naphthyl-B(OH)$_2$ | First synthesis method |
| Example Compound No. A48 | 2-bromo-7-iodo tris(9,9-dimethylfluorene) structure | 2-naphthyl-B(OH)$_2$ | phenyl-B(OH)$_2$ | Second synthesis method |
| Example Compound No. A26 | 2-bromo-7-iodo bis(9,9-dimethylfluorene) structure | 2-naphthyl-B(OH)$_2$ | 2-naphthyl-B(OH)$_2$ | Second synthesis method |

Note 1:
First through third synthesis methods are described below.
First synthesis method:
a method of coupling a 2,7-dibromo modification of oligofluorene to a 2-naphthylboronic acid derivative.
Second synthesis method:
a method of coupling a 2-bromo-7-iodo modification of oligofluorene to two kinds of arylboronic acid derivatives.
Third synthesis method:
a method of coupling a 2-monobromo modification of oligofluorene to a 2-naphthylboronic acid derivative.

Comparative Example 1

4,4,'-N,N'-dicarbazol-biphenyl (CBP) was used as a Comparative Compound.

A thin film was formed by vapor co-depositing the CBP and Ir(ppy)$_3$, which is a sensitizer, at a weight mixing ratio of 75:25. A phosphorescence spectrum of the formed thin film was then measured and a triplet excitation energy was found in the same manner as in Example 1. The result is shown in Table 3.

An absorption spectrum of the thin film obtained by vapor depositing the CBP alone was measured in the same manner as in Example 1 and an energy gap was found in the same manner as in Example 1. The result is shown in Table 3.

A glass transition temperature of the CBP was measured in the same manner as in Example 1 by using a DSC. The result is shown in Table 3.

TABLE 3

| | Example 1 | Example 2 | Comparative Example 1 |
|---|---|---|---|
| Compound | Example Compound No. A21 | Example Compound No. A61 | CBP |
| Glass transition temperature | 180° C. | 187° C. | 80° C. |
| Molecular weight (g/mol) | 638 | 831 | 484 |
| Singlet energy | 2.99 eV | 2.87 eV | 3.4 eV |
| Triplet energy | 2.1 eV | 2.16 eV | 2.67 eV |

Example 3

Fabrication of Organic EL Element

An organic EL element shown in FIG. 1 was fabricated. First, a transparent electrode 16 was produced on a glass substrate (transparent substrate 17) by patterning indium tin oxide (ITO). In this case, the thickness of the transparent electrode 16 was 100 nm and the electrode surface area was 3.14 mm$^2$.

Then, the below-described constituent materials of the organic layer and electrode layer were resistance heated and vacuum vapor deposited in a vacuum chamber under 10$^{-4}$ Pa to continuously form the films and fabricate an organic EL element. More specifically, first, the compound HTL1 as shown below was vacuum deposited to form a hole transport layer 15. The thickness of the hole transport layer was 40 nm. Then, the Example Compound No. A61 as a host, Example compound No. X1 as a first dopant, and the below-described compound Ir(ppy)$_3$ as a second dopant were vapor co-deposited at a weight concentration ratio of 80:4:16 to form a light-emitting layer 14. The thickness of the light-emitting layer 14 was 25 nm. Then, the below-described compound Bphen was vapor deposited to form an electron transport layer 13. The thickness of the electron transport layer 13 was 50 nm. The material KF was vapor deposited as a first metal electrode layer 12. The thickness of the metal electrode layer 12 was 1 nm. Al was deposited as a second metal electrode layer. The thickness of the metal electrode layer 11 was 100 nm.

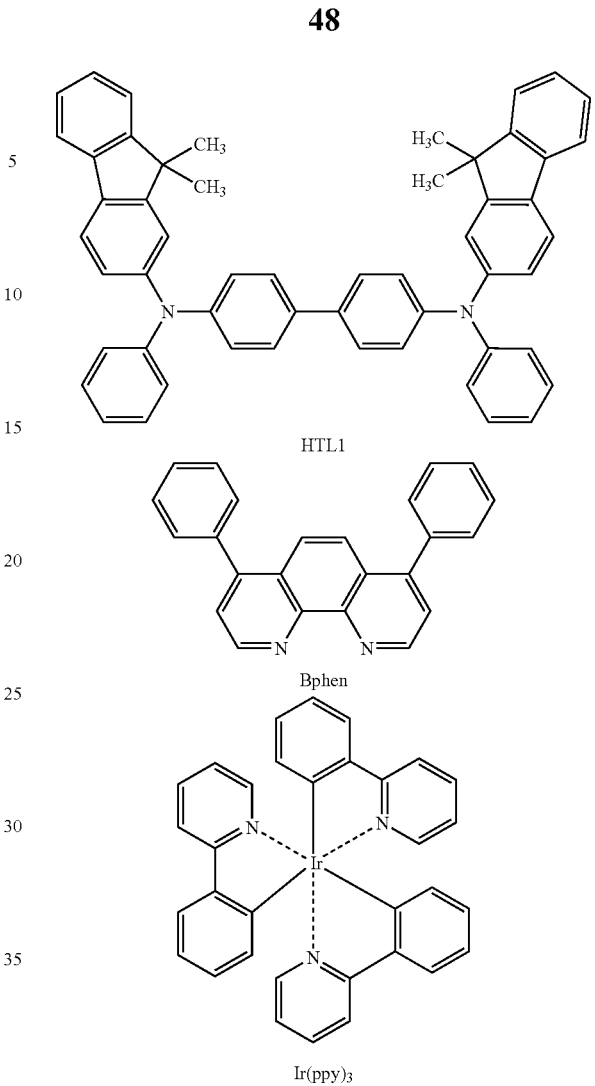

HTL1

Bphen

Ir(ppy)$_3$

An organic EL element was fabricated in the above-described manner. Properties of the obtained organic EL element were evaluated. The results are shown in Table 4. The specific evaluation methods are described below.

(1) Applied Voltage, Current Density, Luminance

Advantest R6144 was used as a current-voltage source and a current value was measured with a multimeter Model 2000 produced by Keithley Instruments Inc. The emission luminance was measured using BM7 produced by Topcon. The current luminance efficiency and light emission efficiency were estimated and evaluated from the current density and luminance obtained by the measurements.

(2) External Quantum Efficiency

An external quantum efficiency was estimated and evaluated from a light emission spectrum of the element by using SR3 manufactured by Topcon.

(3) Half-Life

Advantest R6144 was used as a constant-current source, and a silicon photodiode S2387-1010R manufactured by Hamamatsu Photonics was used to detect the emission of light. The luminance observed when a current of 100 mA/cm$^2$ was supplied to the element was taken as the initial luminance, and a time required for the value of the initial luminance to reduce by half was taken as the half-life.

Example 4

An organic light-emitting element was fabricated by the same method as in Example 3, except that Example Compound No. A61 as a host and Example Compound No. X1 as a dopant that were used in Example 3 were vapor co-deposited to obtain a weight concentration ratio of 88:12 and form a light-emitting layer 14. The element obtained was evaluated in the same manner as in Example 3. The results are shown in Table 4.

Example 5

An organic light-emitting element was fabricated by the same method as in Example 3, except that Example Compound No. A61 as a host, Example Compound No. X3 as a first dopant, and Ir(ppy)$_3$ as a second dopant that were used in Example 3 were vapor co-deposited at a weight concentration ratio of 72:12:16 to form a light-emitting layer 14. The element obtained was evaluated in the same manner as in Example 3. The results are shown in Table 4.

Example 6

An organic light-emitting element was fabricated by the same method as in Example 3, except that Example Compound No. A61 as a host and Example Compound No. X3 as a first dopant that were used in Example 3 were vapor co-deposited at a weight concentration ratio of 88:12 to form a light-emitting layer 14. The element obtained was evaluated in the same manner as in Example 3. The results are shown in Table 4.

TABLE 4

| | Applied voltage @ 0.1 mA/cm$^2$ (V) | Current density @ 4 V (mA/cm$^2$) | Current Luminance efficiency (Cd/A) | Light emission efficiency (1 m/W) | Voltage @ 1000 cd/m$^2$ (V) | Voltage @ 2000 cd/m$^2$ (V) | External quantum yield (%) | Half-life (h) | Initial luminance @ 100 mA/cm$^2$ (cd/m$^2$) |
|---|---|---|---|---|---|---|---|---|---|
| Example 3 | 2.6 | 70.9 | 9.1 | 8.8 | 3.2 | 3.5 | 12 | 700 | 7000 |
| Example 4 | 2.5 | 83.0 | 6.8 | 6.8 | 3.1 | 3.4 | 10 | 800 | 4500 |
| Example 5 | 2.6 | 57.8 | 15.3 | 14.7 | 3.3 | 3.6 | 14 | 400 | 9000 |
| Example 6 | 2.5 | 70.5 | 8.1 | 7.8 | 3.2 | 3.7 | 12 | 300 | 7000 |

Accordingly, the organic EL elements fabricated according to these examples provide relatively long life emission of high efficiency at a relatively low voltage.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-284830, filed Nov. 1, 2007, which is hereby incorporated by reference herein in its entirety.

What is claimed is:

1. An oligofluorene compound represented by a General Formula (2) below:

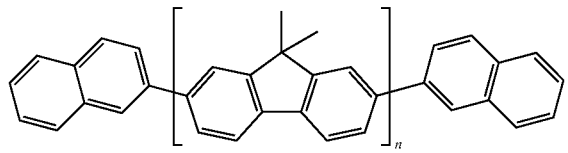

wherein in Formula (2), n represents an integer of 2 to 4.

2. An organic EL element comprising an anode and a cathode; and an organic thin-film layer sandwiched between the anode and the cathode, wherein the oligofluorene compound according to claim 1 is contained in the organic thin-film layer.

3. The organic EL element according to claim 1, wherein the organic thin-film layer comprises a light-emitting layer;

the light-emitting layer comprises a host and a guest; and the host is the oligofluorene compound, and the guest is a phosphorescent light-emitting dopant.

4. The organic EL element according to claim 3, wherein the phosphorescent light-emitting dopant is a compound represented by a General Formula (3) below

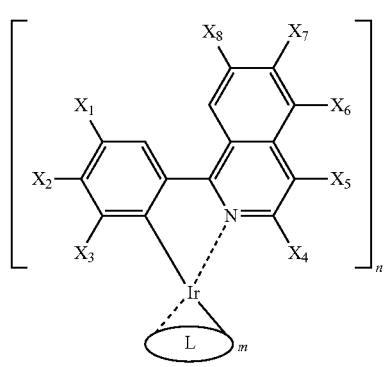

wherein in Formula (3)
X$_1$ to X$_8$ each represent a hydrogen atom, an alkyl group, a halogen atom, or an alkoxy group;
n is 2 or 3;
m is 0 or 1; and
L is a ligand represented by a General Formula (4) or (5) below

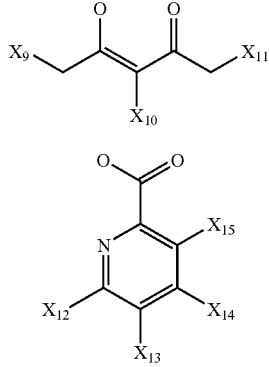

wherein in Formulas (4) and (5) X$_9$ to X$_{15}$ each represent a hydrogen atom, an alkyl group, a halogen atom, or an alkoxy group.

5. The organic EL element according to claim 3, wherein the phosphorescent light-emitting dopant is a compound represented by a General Formula (6) below

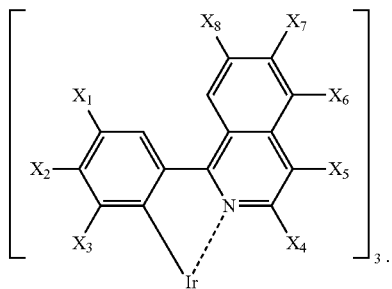

6. The organic EL element according to claim 3, wherein the phosphorescent light-emitting dopant is a compound represented by a General Formula (7) or (8) below

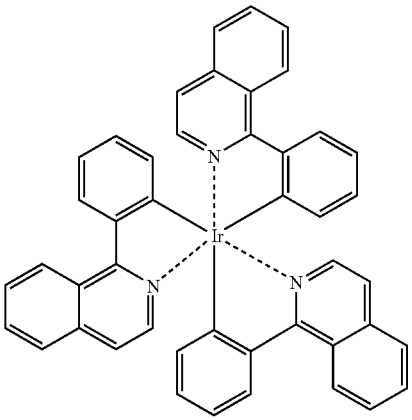

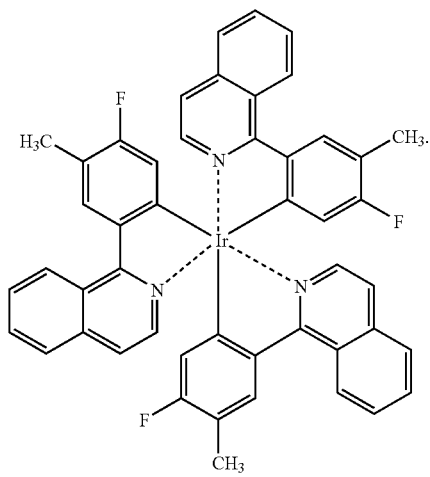

7. The organic EL element according to claim 3, wherein the guest comprises a plurality of phosphorescent light-emitting dopant.

8. The organic EL element according to claim 2, further comprising a color filter.

9. An apparatus comprising a substrate and the organic EL element according to claim 2.

* * * * *